(12) United States Patent
Lading et al.

(10) Patent No.: US 11,337,657 B2
(45) Date of Patent: May 24, 2022

(54) DYNAMIC CALIBRATION OF A BLOOD PRESSURE MEASUREMENT DEVICE

(71) Applicant: PHILIPS HEALTHCARE INFORMATICS, INC., Cambridge, MA (US)

(72) Inventors: Lars Lading, Roskilde (DK); David Boettcher Baek, San Diego, CA (US)

(73) Assignee: PHILIPS HEALTHCARE INFORMATICS, INC., Cambridge, MA (US)

( * ) Notice: Subject to any disclaimer, the term of this patent is extended or adjusted under 35 U.S.C. 154(b) by 1347 days.

(21) Appl. No.: 15/191,817

(22) Filed: Jun. 24, 2016

(65) Prior Publication Data
US 2017/0367659 A1 Dec. 28, 2017

(51) Int. Cl.
*A61B 5/00* (2006.01)
*A61B 5/021* (2006.01)
(Continued)

(52) U.S. Cl.
CPC .......... *A61B 5/7225* (2013.01); *A61B 5/021* (2013.01); *A61B 5/02108* (2013.01); *A61B 5/11* (2013.01);
(Continued)

(58) Field of Classification Search
CPC ............. A61B 5/0205; A61B 5/02125; A61B 2560/0261
See application file for complete search history.

(56) References Cited

U.S. PATENT DOCUMENTS

| 4,873,987 A | 10/1989 | Djordjevich et al. |
| 6,017,313 A | 1/2000 | Bratteli et al. |
| (Continued) | | |

FOREIGN PATENT DOCUMENTS

| EP | 0060116 A1 | 9/1982 |
| JP | 2012061131 A | 3/2012 |
| WO | 2007024777 A2 | 3/2007 |

OTHER PUBLICATIONS

McCombie D.B., et al., "Development of a wearable blood pressure monitor using adaptive calibration of peripheral pulse transit time measurements", Massachusetts Institute of Technology, Dept. of Mechanical Engineering, 2008, pp. 157-159.
(Continued)

*Primary Examiner* — Tse W Chen
*Assistant Examiner* — Michael A Catina

(57) ABSTRACT

Various embodiments enable calibrating a non-invasive blood pressure measurement device by determining multiple parameters defining a stress-strain relationship of an artery of a patient. The device may obtain output signals from a blood pressure sensor at two or more measurement elevations. The obtained measurement signals may be filtered into AC and quasi-DC components, and results fit to exponential functions to calculate an arterial time constant and a venous time constant related to vein draining/filling rates. The arterial and veinous time constants may be used to calculate an infinity ratio. The infinity ratio and the obtained sensor output may be used to calculate values for multiple parameters defining a stress-strain relationship of a measured artery. Once defined, this stress-strain relationship may be stored and applied to future sensor output signals (e.g., blood pressure measuring sessions) to infer patient blood pressure.

18 Claims, 10 Drawing Sheets

(51) Int. Cl.
*A61B 5/11* (2006.01)
*A61B 8/04* (2006.01)
*A61B 8/00* (2006.01)
*A61B 5/024* (2006.01)
*A61B 5/053* (2021.01)

(52) U.S. Cl.
CPC ............ *A61B 5/1121* (2013.01); *A61B 5/681* (2013.01); *A61B 5/6804* (2013.01); *A61B 5/725* (2013.01); *A61B 5/7275* (2013.01); *A61B 5/7282* (2013.01); *A61B 8/04* (2013.01); *A61B 8/58* (2013.01); *A61B 5/02416* (2013.01); *A61B 5/053* (2013.01); *A61B 5/6824* (2013.01); *A61B 5/6826* (2013.01); *A61B 5/6828* (2013.01); *A61B 5/6829* (2013.01); *A61B 5/6898* (2013.01); *A61B 2560/0223* (2013.01); *A61B 2560/0238* (2013.01); *A61B 2560/0475* (2013.01); *A61B 2562/02* (2013.01); *A61B 2562/0219* (2013.01); *A61B 2562/0233* (2013.01); *A61B 2562/0247* (2013.01)

(56) References Cited

U.S. PATENT DOCUMENTS

| | | | |
|---|---|---|---|
| 7,674,231 B2 | 3/2010 | McCombie et al. | |
| 8,200,321 B2 | 6/2012 | McCombie et al. | |
| 8,672,854 B2 | 3/2014 | McCombie et al. | |
| 8,777,862 B2 | 7/2014 | Finburgh et al. | |
| 2015/0327784 A1* | 11/2015 | Lading ................ | A61B 5/0082 600/485 |

OTHER PUBLICATIONS

Dentinger A.M., et al., "Sensitivity of Compliance-based Continuous Non-invasive Blood Pressure Monitoring to Changes in Viscoelastic Parameters", IEEE 37th Annual Northeast Bioengineering Conference (NEBEC), Apr. 1, 2011, XP031873699, DOI: 10.1109/NEBC.2011.5778634, ISBN: 978-1-61284-827-3, pp. 1-2.

International Search Report and Written Opinion—PCT/US2017/034209—ISA/EPO—Aug. 17, 2017.

International Application No. PCT/US2017/034209, "International Preliminary Report on Patentability" dated Jan. 3, 2019, 9 pages.

\* cited by examiner

DYNAMIC CALIBRATION OF A BLOOD PRESSURE MEASUREMENT DEVICE

BACKGROUND

Devices for measuring cardiovascular properties suffer from the problem that the measurement itself interferes strongly with the state of the subject, thereby leading to erroneous results. Current cuff-based methods that may impart a significant physiological impact. In current cuff-based methods, the systolic blood pressure is obtained by constricting an artery, which in most cases is the brachial artery in the upper arm. Constricting the artery affects pulse pressure propagation and pulse pressure shapes, which may only be tolerated in the peripheral system. Further, the diastolic pressure is derived from measurements obtained when the transmural pressure (pressure difference between the outside and the inside of an artery) is close to zero, which implies those measurements are made under conditions that are far from normal.

In addition, traditional methods based on inflatable cuffs and measurements performed in a clinical environment may have strong psychological effects causing changes in a patient's blood pressure. For example, the psychological effects of being in clinical environment may cause an elevation in the patient's blood pressure. The phenomenon is commonly called "white coat syndrome" or "white coat hypertension." In an additional example, a patient's blood pressure may be elevated during normal daily activities but not in a clinical environment. This phenomenon is commonly called "masked hypertension."

Additionally, blood pressure often exhibits considerable variability over time. Thus, identifying diurnal or other temporary variations in blood pressure may be important for proper diagnosis of hypertension, detection of sepsis, and determination of central cardiovascular properties. It has also recently been shown that performing ambulatory blood pressure measurements may present cost-savings over "as needed" or ad hoc blood pressure measurements, because ambulatory blood pressure measurements may enable early detection of hypertension and resultant reduced treatment costs.

SUMMARY

The various embodiments may include methods, devices for implementing the methods, and non-transitory processor-readable storage media comprising instructions causing the processor to execute operations comprising the methods for calibrating a blood pressure measurement device using a ratio of an arterial time constant to a veinous draining/filling time constant, which is referred to as an "infinity ratio." Various embodiments may include a method of calibrating a blood pressure measurement device that is positioned on a subject's body by obtaining, from one or more sensors of the blood pressure measurement device, two or more measured pulses, wherein at least two measured pulses from the two or more measured pulses correspond to different elevations of the blood pressure measurement device, determining an arterial time parameter and veinous time parameter based on the two or more measured pulses, determining a hydrostatic pressure change based on differences between the different elevations, and determining a stress-strain relationship based on the arterial time parameter, veinous time parameter and the hydrostatic pressure change.

Some embodiments may include determining an infinity ratio based on the arterial time parameter and the veinous time parameter, and in such embodiments determining the stress-strain relationship may be based on the infinity ratio and the hydrostatic pressure change.

Such embodiments may include determining a current mean arterial pressure, which may be based at least in part on the stress-strain relationship, determining a pulse pressure, which may be based at least in part on the stress-strain relationship and variation in pressure between the two or more different elevations of the blood pressure measurement device, determining a diastolic blood pressure and a systolic blood pressure, which may be based on the current mean arterial pressure and the pulse pressure, and storing the stress-strain relationship, the current mean arterial pressure, the pulse pressure, the diastolic blood pressure, the systolic blood pressure or any combination thereof.

In such embodiments, the two or more measured pulses may be measured using one or more of bioimpedance, impedance plethysmography, photoplethsmography, ultrasound, or any combination thereof.

In such embodiments, determining the veinous time parameter may include filtering the two or more measured pulses using a low-pass filter, identifying a portion of the low-pass filtered two or more measured pulses corresponding to a transition between measurement elevations, fitting an exponentially decaying function to the identified portion of the low-pass filtered two or more measured pulses, and determining the veinous time parameter based on the exponentially decaying function.

In such embodiments, determining the arterial time parameter may include filtering the two or more measured pulses using a high pass filter, determining a diastole portion of the high-pass filtered two or more measured pulses, fitting an exponentially decaying function to the diastole portion of the high-pass filtered two or more measured pulses, and determining the arterial time parameter based on the exponentially decaying function.

In such embodiments, the two or more different elevations of the blood pressure measurement device may include a first elevation at or below a heart level of a subject and a second elevation lower may include height than the first elevation.

In such embodiments, the infinity ratio may be calculated for each group of measured pulses associated with a particular elevation.

In such embodiments, the infinity ratio may be calculated as an average based on the infinity ratio calculated for each of the two or more different elevations.

Further embodiments may include a blood pressure measurement device having one or more arterial measurement sensors, one or more elevation sensors, and one or more processors configured with processor-executable instructions to perform operations of the methods described above. Further embodiments may include a blood pressure measurement device having means for performing functions of the methods described above. Further embodiments include a non-transitory processor-readable storage medium on which is stored processor-executable instructions configured to cause a processor to perform operations of the methods described above.

BRIEF DESCRIPTION OF THE DRAWINGS

The accompanying drawings, which are incorporated herein and constitute part of this specification, illustrate exemplary embodiments of the claims, and together with the general description given above and the detailed description given below, serve to explain the features of the claims.

DETAILED DESCRIPTION

Figure 1A:
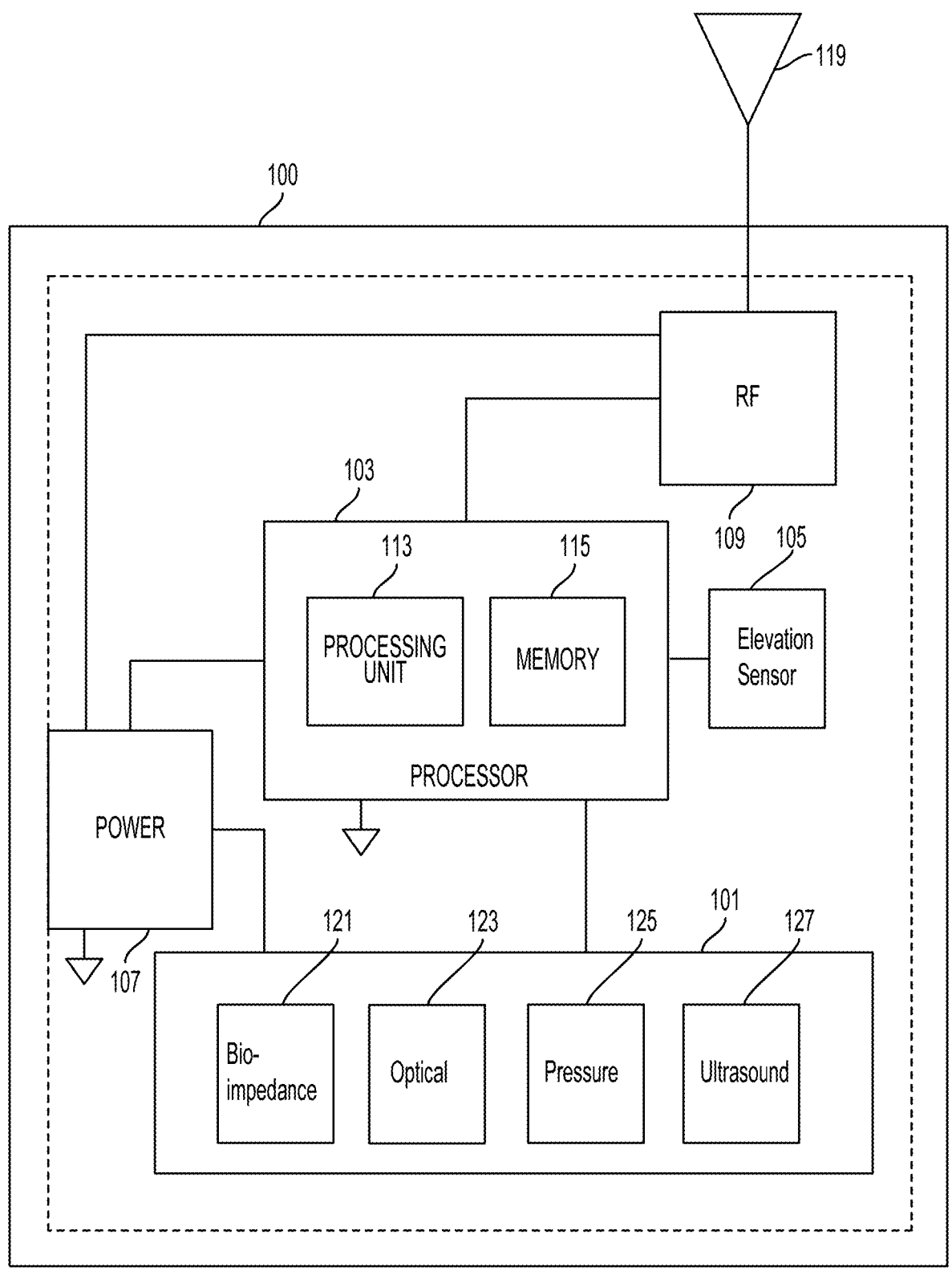
FIG. 1A is a block diagram of an embodiment system including an embodiment blood pressure measurement device placed on a subject.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

Various embodiments may include calibrating a blood pressure measuring device by measuring quantities proportional to arterial distension and vein filling/draining rate, and using the measurements to determine multiple parameters defining a stress-strain relationship of an artery or vein of a patient. The multiple parameters defining the stress-strain relationship may be applied to future device measurements to infer a patient's blood pressure. In some implementations, determining the multiple stress-strain parameters may include obtaining sensor output signals at two or more measurement locations (e.g. different elevations of the patient's extremity). The obtained measurement signals may be filtered and used to calculate an infinity ratio representing a relationship between the time constant (i.e. arterial time constant) and a vein draining/filling rate (i.e., veinous time constant). The infinity ratio and the obtained sensor output may be used to calculate values for multiple parameters defining a stress-strain relationship associated with a patient's pulse. Once defined, this stress-strain relationship may be stored and applied to future sensor output signals (e.g., blood pressure measuring sessions) to infer patient blood pressure.

The terms "blood pressure measurement device", "blood pressure monitoring device", and "non-interfering blood pressure measurement device" may be used herein to refer to devices having integrated biometric sensors for reading signals that may be used to determine a patient's blood pressure. Such devices may include a negligible interfering and negligible perception configuration or form blood pressure measurement device (e.g., a wearable patch, bracelet, anklet, watch, etc.). Such devices may further include biometric blood pressure measurement sensors integrated into furniture, clothing, office accessories, and other items with which the patient's extremities come into contact. Non-interfering blood pressure measurement devices may include biometric sensors that are configured to obtain measurements without constricting, deforming, or contorting a patient's limb.

The various embodiments provide methods and devices implementing the methods for dynamic non-invasive calibration of blood pressure monitoring devices with a minimum of interference to the measurement. The various embodiments may enable non-interfering measurements of blood pressure.

In various embodiments, a blood pressure measurement device may include one or more biometric sensors that provide a measurement signal. The measurement signal may be a sensor output that varies proportionally with the variations of the cross-sectional area of an artery at a location of the measurement (i.e., arterial distension). In some embodiments, the linearity may be for incremental changes or fluctuations and not for the absolute values because of the impact of other tissues such as veins and muscles, and due to the bias terms discussed further below. The various embodiments may provide outputs associated with the area or lumen of an artery, and thus to the square of the diameter. Cross-sectional area and lumen (volume) may be proportional because expansion in the direction of the artery may be negligible. The placement of the blood pressure measurement device and/or the location of the measurement may be at any location on an extremity of a patient, such as an arm, wrist, finger, leg, ankle, etc. of the patient. In various embodiments, the blood pressure measuring device may be unattached to the extremity, such as when the device is one or more sensors integrated into furniture. In such embodiments, sensors within the blood pressure measurement device may be positioned or oriented such that they may contact the extremity of a patient.

The various embodiments may measure arterial lumen or cross-sectional area with a bias term. In order to convert such measurements to pressure, the sensitivity of blood pressure measuring device, as well as the arterial stiffness, may be needed and a bias term may be determined. In the various embodiments, variations of the hydrostatic pressure (for example an elevation difference of 60 cm may correspond to a 47 mmHg pressure change, while the Mean Arterial Pressure at heart level may be around 100 mmHg) may be continuously monitored along with outputs from an elevation sensor, such as a 3D accelerometer with measurements integrated in order to detect position changes, a high resolution barometer configured to output the elevation or change in elevation of the measuring location, etc. When the pulse rate is constant, the "driving pulse pressure" may be assumed to be unchanged and the pulse pressure may be assumed to be constant, and thus the only pressure change may be caused by the change of the hydrostatic pressure due to changes in elevation of the measuring location. This presumption may enable a method of calibration for incremental changes.

The absolute pressure may be evaluated through analysis and comparison of both the exponential decay of the diastolic part of the pulse (i.e., the last part of the pulse) and the exponential decay of a pulse signal attributed to vein filling time. A fitting procedure executed on both the diastolic pulse and the veinous signal may give the arterial pulse and veinous filling decay constants and the correction to the bias term. Thus, in the various embodiments both pulse pressure and mean arterial pressure may be estimated. Using these estimates, systolic and diastolic pressures may be determined with a temporal resolution unattainable by traditional cuff-based devices and without any interference of the artery on which measurements may be performed. Additionally, the various embodiments may eliminate the need for measuring local Pulse Wave Velocity and arterial diameter to determine blood pressure.

In the various embodiments, variations of the measured quantity may vary proportionally with the variations of the cross-sectional area of the artery with inclusion of an unknown additive bias term. The arterial time constant, the veinous time constant, and the infinity ratio defining a relationship between the time constants and the bias may change, but typically over time scales much longer than the duration of a single pulse. The duration of a single pulse is typically about one second, but the length of a single pulse may vary over time and from individual to individual.

The arterial pressure P and the artery cross-sectional area may be related by a stress-strain relation that generally may be assumed to be exponential. The pressure pulses associated with heartbeats may be smaller than the mean pressure and a local linear relation between pressure variations and cross-sectional area variations of the artery can be assumed. The gradient of this relation may define the instantaneous incremental arterial stiffness or elasticity. The stiffness may not be constant, and the stiffness may continuously adapt to the state of the subject (i.e., patient). The response time of changes in arterial stiffness or elasticity may typically be in the order of minutes or longer, but may be much shorter in cases of extraordinary changes of the environment to which the subject is exposed. Incremental pressure may be related to lumen changes by the gradient of the stress-strain relation. In general, the lumen and the cross-sectional area of peripheral arteries may be proportional since the variations in the direction of the artery may be negligible. The elastic properties of peripheral arteries may be predominantly given by smooth muscles arranges in a spiral pattern—presumably arranged in such a way that the arterial expansion upon a pressure increase predominantly may be in the radial direction and negligible in the longitudinal direction. At low pressures the arterial vessel may be very elastic because it is primarily composed of elastin fibers. However, at higher pressures, the arterial vessel may be stiffer, because the properties due to the impact of smooth muscles.

Similarly, the impact of incremental variations in cross-sectional lumen of neighboring veins on arterial distension may be represented by the gradient of a portion of the pulse signal attributed to veinous distension. Veinous tissues may be ten times more elastic than corresponding arterial tissue and thus incremental changes to lumen cross-section may occur more slowly than in arteries. These changes may be attributed to the filling and draining of veins as an affected extremity changes elevation. Incremental pressure and lumen changes may be related by the gradient of the portion of the signal obtained from the sensor that is attributed to veinous distension. A veinous decay constant (i.e., the gradient of the signal) may be larger for veins than for arteries.

In the various embodiments, the pressure pulse occurring after each contraction of the left heart ventricle can be considered to include three parts. The first part may be the immediate rise of pressure as a consequence of the ejection from the heart, i.e., the systole phase. The second part may include an exponentially decaying pressure occurring in the diastole phase the second phase may be terminated by the occurrence of the subsequent pulse. The exponential decay may be caused by the arterial system being connected with the veins through capillary network with a high fluid-flow resistivity and the veins being much more elastic than the arteries. Thus, the veinous system may essentially behave in a manner that can be represented as a capacitor much larger than the capacitor representing arteries. Propagation effects may play an insignificant role for the decay since the time constant of the decay may be much larger than the pulse propagation time through the arterial system. The third part may represent reflections from discontinuities in the arterial system such as bifurcations or diameter changes in the arterial system, particularly in the vicinity of a sensor.

In the various embodiments, the pulse rate averaged over time, such as averaged over about one minute of measurements, may play an important role in calculating blood pressure based on sensor measurements. The relationship between pulse rate and blood pressure is in general ambiguous. However, it may be assumed that if the heart rate is constant—except for the very short term heart rate variability—then the pulse pressure may also be constant and the only change in the measured blood pressure may be caused by a change of the hydrostatic pressure.

The hydrostatic pressure affecting the blood pressure in an artery may be exclusively given by the elevation of an arterial segment within an extremity of a patient relative to a reference point if it is assumed that the fluid in the system is incompressible, i.e. its density is constant, and that the gravitation acceleration is constant. The change in hydrostatic pressure $P_h$ encountered by moving a measuring location from one position to another position separated by a distance h in the direction of gravity (i.e., height) may simply be given by:

$$\Delta P_h = \rho g \Delta h \quad (1)$$

where ρ is the density of the fluid and g is the gravitational acceleration. For example, the difference in hydrostatic pressure at the wrist of an arm of length 60 cm lowered to a straight downward position and a horizontal position, respectively, may be 47.4 mmHg, which may be significant relative to the mean arterial pressure at the elevation of the heart (typically around 100 mmHg). The siphon effect may be neglected if the fluid system is terminated into a very high fluid impedance unit, which is the case for most of the arterial systems in which the high resistance capillary network provides the connection from arteries to veins.

The systems, methods, and devices implementing those methods of the various embodiments may enable calibration of a blood pressure measurement device based on measured electrical impedance (or admittance, i.e., the inverse of impedance) as a function of time. The various embodiments may continuously estimate blood pressure based on measured electrical impedance as a function of time by continuously adapting to changes of the arterial and veinous properties of a patient (i.e., subject) in such a way that no special action may be required by the patient and no sensation may be felt by the patient.

In various embodiments, a blood pressure measurement device may initially be calibrated for the correct arterial properties when a measuring session is started. In various embodiments, a blood pressure measurement device may initially be calibrated in a manner that may enable the blood pressure measurement device to be set for the correct arterial and veinous properties for a patient at an initial time.

In an embodiment, a blood pressure measurement device may be calibrated to measure a quantity (X) monotonically related to the cross sectional area (A) of an artery arranged in the vicinity of a sensor of the blood pressure measurement device by: attaching the blood pressure measurement device to a extremity (e.g. arm, wrist, finger, etc.) of a subject such that the sensor is arranged in the vicinity of an artery in the extremity of the subject; placing the extremity of the subject into at least two positions with the first elevation being at or below heart level and subsequent elevations being lower than the initial elevation so that the measurement location of the sensor arrives at z different heights with regard to a reference height; at each of the z different heights, measuring and recording the average value of the output of the sensor; separating the sensor output into an alternating current (AC) and quasi-direct current (DC) component signals; filtering the change in quasi-DC signal to determine a veinous filling/draining rate (i.e., veinous time constant) and the AC signal to determine the pulse decay (i.e., the arterial time constant); calculating an infinity ratio that relates the arterial pulse decay time constant to the veinous time constant; using the known effect of the hydrostatic force at the different heights of the measurement location of the sensor and the infinity ratio to calculate two or more unknown parameters of a stress-strain relationship associated with the arterial distension; and using the stress-strain relationship to determine an absolute blood pressure. In various embodiments, the "quasi-DC signal" may be the AC signal below the pulse rate (i.e., 1 Hz). The AC signal contains frequency components above 1 Hz and may be used to determine the pulse decay time constant.

In the various embodiments, a sensor, such as an arterial measurement sensor, may provide an output, X, that is proportional to the instantaneous arterial cross-sectional area, but that may also include an unknown additive bias term. The variations of the sensor output may provide the equivalent variations of the arterial cross-section as impacted by variations in vein cross-section. One problem to be solved involves converting the sensor output to properly calibrated blood pressure. This conversion may vary over time because of the varying arterial stiffness. A measuring bias may change as a consequence of movements of the extremity on which the measurement is performed, which may correspond to elevation changes at the measurement site. A change in bias may also be attributed to movement of the measurement device with reference to the underlying limb or a loss of sensor connectivity. Bias changes may not occur on time scales corresponding to the filling or draining time of veins in proximity of an artery with elevation changes. The incremental conversion from sensor signal to lumen may also change as a consequence of changing posture/position of the patient.

In the various embodiments, an elevation sensor may provide an output that may be continuously converted to a measure of the elevation of the measuring location. For example, the elevation sensor may be a three-dimensional (3D) inertial sensor such as an accelerometer, where elevation changes may be inferred from integration of the accelerometer output. Other examples of elevation sensors include a barometer and/or a magnetic near-field device, but elevation sensors may be any other type sensor configured to measure of the elevation or changes in elevation of the measuring location.

Individual pulses may exhibit considerable variability in amplitude, pulse shape and pulse length. In order to obtain a characteristic pulse, conditional averaging may be applied in various embodiments. A conditional average may be obtained by averaging a set of numbers in which a given condition has to be fulfilled for each of the numbers. In an embodiment, conditional averages may be the amplitudes X $(t_{i,j})$ in which the first index i represents a fixed time from a reference time of the pulse. The reference time may be defined by the time in which the largest positive slope of the pulse is observed. For example, the reference time may be at the first zero-crossing of the high-pass filtered pulse. If a number of pulses are recorded, the second index j may be the pulse number. In an embodiment, each of the i values of a pulse may be averaged over all pulses, that is over j. The result may be a pulse representing the average pulse averaged over all recorded pulses.

In an embodiment, a method for calibrating a blood pressure measurement device may include selecting a location on the body for the measurement, such as a wrist, a finger, or some other location where arteries are identified. The selected location may be fitted with a blood pressure measurement device including an arterial measurement sensor, such as a non-interfering sensing device. The arterial measurement sensor may measure a quantity proportional to the distension of the artery right below the sensor and an elevation sensor, such as a 3D inertial sensor, which may be supported by a tilt sensor. In an embodiment, the outputs of the sensor (e.g., the arterial measurement sensor), and the elevation sensor may be recorded continuously. The pulse rate may be measured and averaged continuously over a sliding window of a width of from 0.5 minute to about 2 minutes. The elevation may be continuously evaluated and averaged over a few seconds.

In various embodiments, the sensor may produce an output (i.e., a distension signal) that relates to arterial lumen distension and may contain contributions from the draining and filling of neighboring veins. The signal may be linearly dependent on arterial lumen/cross-section and lumen of veins in proximity to the artery. Sensor output may be recorded for measurements taken when the patient's extremity is positioned at two or more elevations. For example, an initial position of the blood pressure measuring device may be at or below the heart level of the patient, and subsequent elevations of the blood pressure measuring device may be below the initial position, such as in a resting position. Elevation of the patient's extremity above the heart level may cause undesirable variations in arterial lumen cross-section that render calculation of an accurate stress-strain relationship difficult, thus measurement elevations may remain at or below a patient's heart level. To reduce the impact of muscle expansion and contraction on the arterial lumen, the extremity to which the blood pressure measurement device is secured may be supported throughout the change in elevation. In some embodiments, the extremity may be supported at heart level and then lowered or allowed to fall into a resting position. In some embodiments, the extremity may be mechanically lowered from heart level to a secondary position so that the rate and elevation may be controlled.

Various embodiments may include separating the sensor output into an AC signal component and a quasi-DC signal component. The sensor output signal component may be subjected to a high pass filter to obtain the AC signal component. An exponential function may be fit to a portion of the AC signal representing a diastolic pulse in order to obtain a time constant representing changes in pressure with time during each pulse due to arteries of the extremity filling and draining in each of the blood pressure measurement device positions. The high-pass filtering may remove the very low frequency part of the signal, that is the DC-level and fluctuations on time scales larger than characteristic pulse lengths. From this high-pass filtering, the arterial time constant may be inferred. The cut-off frequency may be 0.5 Hz, 1 Hz, 2 Hz or some value within this range. Low-pass filtering may also be incorporated in a blood pressure measurement device in order to reduce noise with a cut-off frequency typically below 100 Hz such as 60 Hz, 40 Hz, 20 Hz or 10 Hz.

In various embodiments, the high-pass filtering may evaluate the pulse amplitudes as the differences of the maximum and minimum of each pulse. In various embodiments, average values for the peak for the accepted pulses may be evaluated. For pulses exhibiting small oscillatory characteristics, this may be given by 0.2 sec after the systolic peak or after the peak following the dicrotic notch until the trough of the pulse.

In various embodiments, the processor may execute a low-pass filter on the sensor output signal to obtain the quasi-DC signal component, which may be analyzed in order to find the steepest gradient. For example, the steepest gradient may occur at the interval between a peak and a trough of a pulse.

The high-pass and low-pass filters may be wavelet filters and may optionally be configured with a mother wavelet tailored to the expected pulse shape, or the filter may be a fixed Finite Impulse Response (FIR) filter or an Infinite Impulse Response Filter (IIR) as known in the art.

In an embodiment, the diastolic parts of measured pulses may be fitted to an exponentially decaying function including an additive bias, i.e. to $$f(t,\alpha,\tau_a,\beta)=\alpha\exp[-t/\tau_a]+\beta \quad (2)$$

where the parameter $\alpha$ is defined by the distension amplitude of the diastolic part of the pulse and $\beta$ is the bias term caused by the possible contributions from tissues other than the artery and by a possible off-set of the measuring electronics. Time is denoted t and the time-constant of the decay is denoted $\tau_a$ which is reflective of the resistance of the capillary network connecting artery with veins in conjunction with the capacity of the arteries.

In an embodiment, measured diastolic parts may have the exponentially decaying function fitted to them and for each individual pulse. The fitting parameters may then be averaged over a series of pulses, such as 60 pulses or any other number of pulses. Alternatively, the fitting of pressure measurements to an exponentially decaying function may be performed on pulses obtained by conditional averaging over a series of pulses, such as up to 60 pulses. The diastole may be defined as starting at the time instance after the first dip of the pulse in which the second derivative of the measured pulse waveform with respect to time is positive and ending at the onset of the subsequent pulse (see FIG. 6).

In various embodiments, the processor of the blood pressure measurement device may validate the exponential fit by comparing a result of $f(t,\alpha,\tau_a,\beta)$ (i.e., eq.1) with the data used for fitting. A normalized correlation value above a preset value may be applied to the result of eq. 1 and, for example, may be 0.8, 0.9, or more. The normalized root means square deviation may also be applied and the normalized deviation may then be 0.2 or less. The output may be a set of parameters characterizing the amplitude, the arterial time constant and the bias that added to the fit would imply an asymptotic value of zero. Additionally time stamps for the validated pulses may be determined. In various embodiments, the arterial time constant may be the time-constant of the decay $\tau_a$ determined from exponential curve fitting of eq. 1 to a number of validated pulses.

Movement of the patient's extremity from one elevation to the next may be assumed to occur within a fraction of a second such as 0.1 sec or 0.2 seconds. A change in the low-frequency signal (i.e., the quasi-DC signal) during the change in elevation may be attributed to filling or draining of veins as a consequence of the change in hydrostatic pressure. As with the high-pass (i.e., AC component) signal, the processor of the measurement device may fit the low-pass (i.e., DC component) signal to an exponentially decaying curve to obtain the veinous time constant $\tau_v$. This time constant will typically be much larger than the time constant for the pulse decay. In various embodiments, the veinous time constant $\tau_v$ may be determined from exponential curve fitting.

Various embodiments may include the calculation of an infinity ratio representing the mathematical relationship between the arterial time constant and the veinous time constant. The infinity ration may be evaluated as the ratio of the arterial time constant to the veinous time constant associated with vein filling or draining. The infinity ratio $\gamma$ may be represented by the expression:

$$\gamma=\tau_a/\tau_v. \quad (3)$$

where $\gamma$ is the infinity ratio, $\tau_a$ is the arterial time constant and $\tau_v$ is the veinous time constant. The infinity ratio may be calculated for each pulse, for multiple pulses, for a number of validated pulses, or as an average of validated pulses for each of the measurement elevations.

Adding the bias term $\beta$ to the distension signal may yield pulses where the decay would approach zero. However, because the pulse decay has an asymptote that is larger than zero, an infinity quantity proportional to the infinity ratio may also be added. This infinity quantity may be expressed by the function:

$$a_\infty=(\delta a+\beta)(1+1/\gamma) \quad (4)$$

where $a_\infty$ is the infinity quantity, $\beta$ is the bias term, $\delta a$ is an incremental change in the arterial cross-section, and $\gamma$ is the infinity ratio. These parameters may be used to define the stress-strain relationship necessary in determining absolute blood pressure.

In various embodiments, a stress-strain relationship may be expressed by:

$$p=a_0c_0(\exp[a/a_0]-1)$$

$$\delta p=c_0\exp[a/a_0]\delta a$$

p: pressure
a: arterial cross-section given in units of sensor output
$\delta p$: pulse pressure
$\delta a$: distension where $c_0$ and $a_0$ are a priori unknown parameters. This equation for p may be referenced as equation 5 and the equation for $\delta p$ may be referenced as equation 6. In various embodiments, the pulse pressure may be independent of elevation. The parameter $a_0$ may be derived from the stress-strain relationship as evaluated for the different elevations of the blood pressure measurement device.

The result of these evaluations may be expressed by the function:

$$a_0=\frac{a_2-a_1}{\ln[\delta a_1/\delta a_2]}. \quad (7)$$

where $\delta a$ is the incremental variation in arterial cross-section associated with the heart beating at a first and second elevation, $a_1$ is the arterial cross-section at the first elevation, and $a_2$ is the arterial cross-section at the second elevation.

The remaining parameter $c_0$ may be derived by the processor of the blood pressure measuring device by again evaluating the stress-strain relation at the different elevations. The differences may be equal to the hydrostatic pressure difference described in eq. 1. The parameter $c_0$ may thus be expressed by the function:

$$c_0 = \frac{\Delta p_h}{a_0(e^{a_1/a_0} - e^{a_2/a_0})} \quad (8)$$

where $\Delta P_h$ is a change in hydrostatic pressure between the first and second elevation, a is the arterial cross-section at the first and second elevations, $a_0$ and $c_0$ are the previously unknown parameters, and $a_0$ has been determined using eq. 7. In various embodiments, the derivation of both parameters may enable definition of the stress-strain relationship for a measured artery and subsequent calculation of the absolute blood pressure based on measurements by the blood pressure measuring device taken on that artery. The parameter $c_0$ may define the slope of the stress-strain relation of the artery at low pressures. At low pressure, the elastic properties on an artery are dominated by elastin tissue of the artery, which does not change over time periods where continuous blood pressures are monitored. Thus, for a given subject and artery, determination of $c_0$ at one instant may be adequate.

In various embodiments, the Mean Arterial Pressure (MAP) may be calculated by the processor of the blood pressure measuring device. The processor may evaluate the stress-strain relationship at the value of a (i.e., arterial cross-section) determined when the extremity is positioned at the height of the patient's heart. The Pulse Pressure (PP) may be calculated by evaluating the incremental variations of the pressure δp corresponding to the incremental variations of the distension δa around the value of a at the height of the heart.

In an embodiment, the systolic blood pressure (SBP) and Diastolic Blood Pressure (DBP) may be determined using the MAP and PP. The following expressions define the relationship between SBP, DBP, MAP, and PP:

MAP=⅓SBP+⅔DBP (9)

PP=SBP−DBP (10)

Continuous measurement instructions to the subject may be feasible at the initialization of a measuring session, as measuring sessions may last 24 hours or longer. Updating the calibration may be needed in the course of a measuring session, which may be achieved by the sensor of the blood pressure measurement device measuring the distension signal, the pulse rate, and the elevation of the measuring location continuously. For continuous calibration, the exact elevation of each position in not required. However, the height difference should be large enough to produce measurable differences of the arterial distension, which may imply height differences of at least 10 cm. Thus, calibration may continue throughout a measurement session in order to improve accuracy of calculated blood pressure while only evaluating $a_0$ as given by Equation (7).

As an example of a blood pressure measuring device that may be used with the various embodiments, a sensor using bioimpedance variations, preferably with a tetrapolar configuration and an electrode configuration as disclosed in WO2012110042A1, may be utilized to determine blood pressure. In another embodiment, bioimpedance measurement electrodes may be applied to a patient in a line right on top of the radial artery and aligned with the direction of the selected artery. At the wrist, the selected artery may be the radial artery or the ulnar artery. A first set of two electrodes may be placed with a separation somewhat larger than the depth at which the artery is embedded in the extremity. At the wrist, the separation distance may be about 1 cm, but the separation may be considerably larger only confined by the length of the extremity. A second set of two electrodes may be placed with a separation that is less than a separation of electrodes in the first set and less than the separation between the electrodes of the first set. The separation of the electrodes of the second set may be at a minimum given by the depth at which the artery is located, but preferably is larger. At the wrist, this may be a separation of from 5 mm to several centimeters. The sizes of the electrodes may be smaller than the separations, such as diameters of 1 mm, 2 mm, or larger. A current oscillating at a frequency, which may be in the range of 10 kHz to 100 MHz, may be injected into the extremity. The magnitude of the current may be in the range of 0.1 μA to 2 mA. With the electrodes arranged in this manner, the field lines associated with the current flowing through tissues may be essentially perpendicular close to the skin, because the skin and the subcutaneous fat have low conductivities, and aligned with the axis of the blood filled artery, because blood has a relatively high conductivity.

FIG. 1A illustrates an example of a blood pressure measurement device 100 that may be placed on a subject, such as a human, suitable for use with the various embodiment. The blood pressure measurement device 100 may include a processor 103 connected to one or more arterial measurement sensors 101, one or more elevation sensors 105, a power source 107, and a radio module 109 connected to an optional antenna. The processor 103 may include one or more processing units 113 and a memory 115.

The one or more arterial measurement sensors 101 may be any type sensor or combination of types of sensors that may measure arterial properties of the subject, either directly or indirectly. Examples of arterial measurement sensors 101 that may be used with the various embodiments include bioimpedance, optical, pressure, and ultrasound sensors. A blood pressure measurement device 100 may have one or multiple sensors of a given type (e.g., bioimpedance, optical, pressure, and ultrasound sensors), or various combinations of different types of sensors (e.g., bioimpedance and/or optical and/or pressure and/or ultrasound sensors). As an example, the one or more arterial measurement sensors 101 may include a bioimpedance measurement sensor 121, such as an impedance plethysmography sensor, that injects an AC current by one set of electrodes and detect the voltage with another set of electrodes to measure bioimpedance of tissue and blood. As another example, the one or more arterial measurement sensors 101 may include optical sensors, such as a photoplethysmographic sensor 123. As another example, the one or more arterial measurement sensors 101 may optionally include a surface pressure sensor 125. As another example, the one or more arterial measurement sensors 101 may include an ultrasound sensor 127 configured to measure dimensions of the lumen of a vein or artery.

The one or more arterial measurement sensors 101 may output measurements of arterial properties to the processor 103 of the blood pressure measurement device 100. The one or more elevation sensors 105 may be any type sensor or combination of sensors that may measure the elevation of the blood pressure measurement device 100 and the extremity or other location of the subject 104 to which the blood pressure measurement device 100 may be in contact. As examples, the one or more elevation sensors may be three dimensional inertial sensors (e.g., accelerometers, etc.), GPS sensors, a high resolution barometric sensor, a near-field magnetic sensor, etc. The one or more elevation sensors 105 may output elevation measurements to the processor 103 of the blood pressure measurement device 100.

In an embodiment, via the radio module 109 and antenna 119, the processor 103 of the blood pressure measurement device 100 may establish a wireless connection with a remote computing device, such as a smart phone. In this manner, via the wireless connection with the computing device, the processor 103 of the blood pressure measurement device 100 may transmit measurement data to and receive commands from another computing device. In some embodiments, the radio module 109 and antenna 119 may be replaced by or in addition to a wired communication link, such as a universal serial bus (USB) connection, to enable wired communications with another computing device.

Various types of computing devices may be used in the various embodiments, including, for example, cellular telephones, smart-phones, web-pads, tablet computers, Internet enabled cellular telephones, WLAN enabled electronic devices, dedicated healthcare electronic devices, and similar electronic devices equipped with at least a processor and configured to communicate with an blood pressure measurement device as described herein.

Figure 1B:
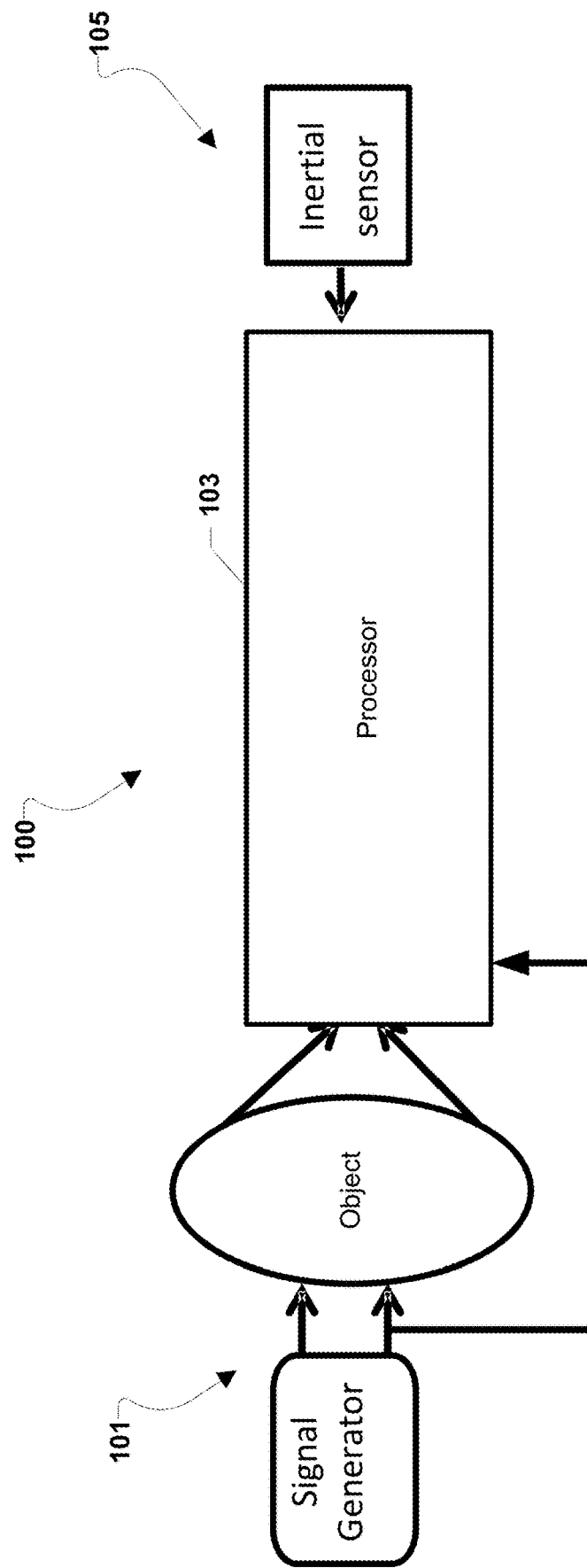
FIG. 1B is a component block diagram of an embodiment blood pressure measurement device.

In some embodiments, the blood pressure measuring device 100 may be configured in the form of, or incorporated into, a patch, a finger sleeve, a wrist cuff, a finger ring, band of a wrist watch, back case of a wrist watch, and/or other form of apparel (i.e., clothing that includes an embodiment of a blood pressure measuring device 100). However, the various embodiments are not limited to implementations that are directly worn by a subject, and may include configurations that place the blood pressure sensor against the skin of the subject. For example, in some embodiments, the blood pressure measuring device 100 may be incorporated into safety belts, steering wheels, armrests, seats and other structures in an automobile, train, airplane, or other vehicle, and configured so that the blood pressure sensor(s) are able to take arterial measurements of a subject. As another example, in some embodiments, the blood pressure measuring device 100 may be incorporated into smart furniture and configured so that the blood pressure sensor(s) contact a subject. As a further example, in some embodiments, the blood pressure measuring device 100 may be incorporated into athletic equipment, such as helmets, racket handles, wrist or headbands, shoes, socks, handle bars, etc., and configured so that the blood pressure sensor(s) are able to take arterial measurements a subject. FIG. 1B is a component block diagram of an embodiment blood pressure measuring device 100 illustrating various modules for determining blood pressure by measuring bioimpedance. Using a bioimpedance sensor as a non-limiting example, an arterial measurement sensor 101 may include a signal generator, such as an oscillator, configured to apply an excitation signal, such as an oscillating current, sinusoidal current, etc., via excitation electrodes to an object, such as an artery, and detection electrodes to measure the resulting voltage and provide the voltage to the processor 103. The elevation sensor 105 may include an inertial sensor that may be configured to output acceleration measurements to the processor 103. Various combinations of current and voltage excitation and measurements may be applied as known in the art.

In an embodiment, the processor 103 of the blood pressure measurement device 100 may measure bioimpedances by controlling the arterial measurement sensor 101 to apply an oscillating current to the excitation electrodes. Outputs from the processor may be pulses and mean arterial pressure (MAP) in units of mmHg or in some other selected pressure unit. For example, the pulses and MAP may be transmitted from the processor 103 via a radio module to a computing device, such as a smartphone, for further processing and/or display.

Figure 2:
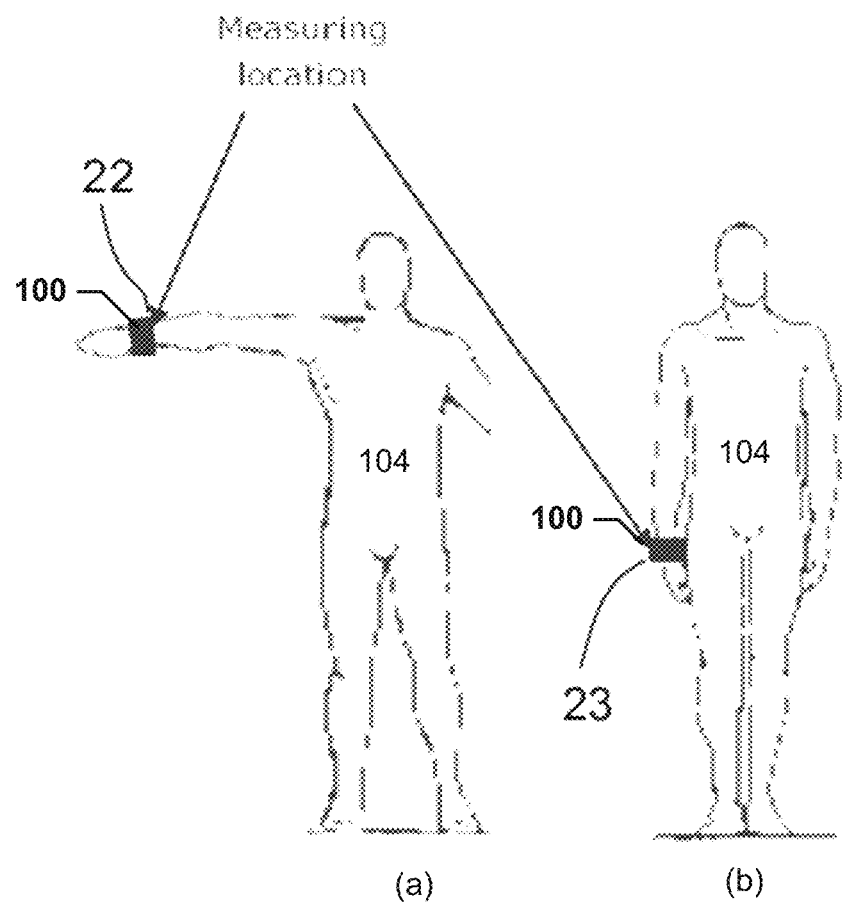
FIG. 2 is a block diagram illustrating movement of a subject's extremity and an embodiment blood pressure measuring device.

In an embodiment, the data from the inertial sensor may be supported by signals from a level detector in such a way that the first and last positions involve a vertical orientation of the extremity (e.g., an arm), and the measurement between involves a horizontal orientation. FIG. 2 illustrates movement of a subject's extremity and an embodiment blood pressure measurement device 100 moving from a first elevation in a horizontal orientation (22), to a second elevation in a straight downward vertical orientation (23). Taking measurements at the two different extremity orientations and knowing the difference in elevation of the sensor during the two measurements enables calculation of blood pressure as described in further detail below. In various embodiments, supporting the limb during the change in elevation may mitigate the effects of skeletal muscle flexion or other tension on arterial and vein cross-sectional properties.

Figure 3A:
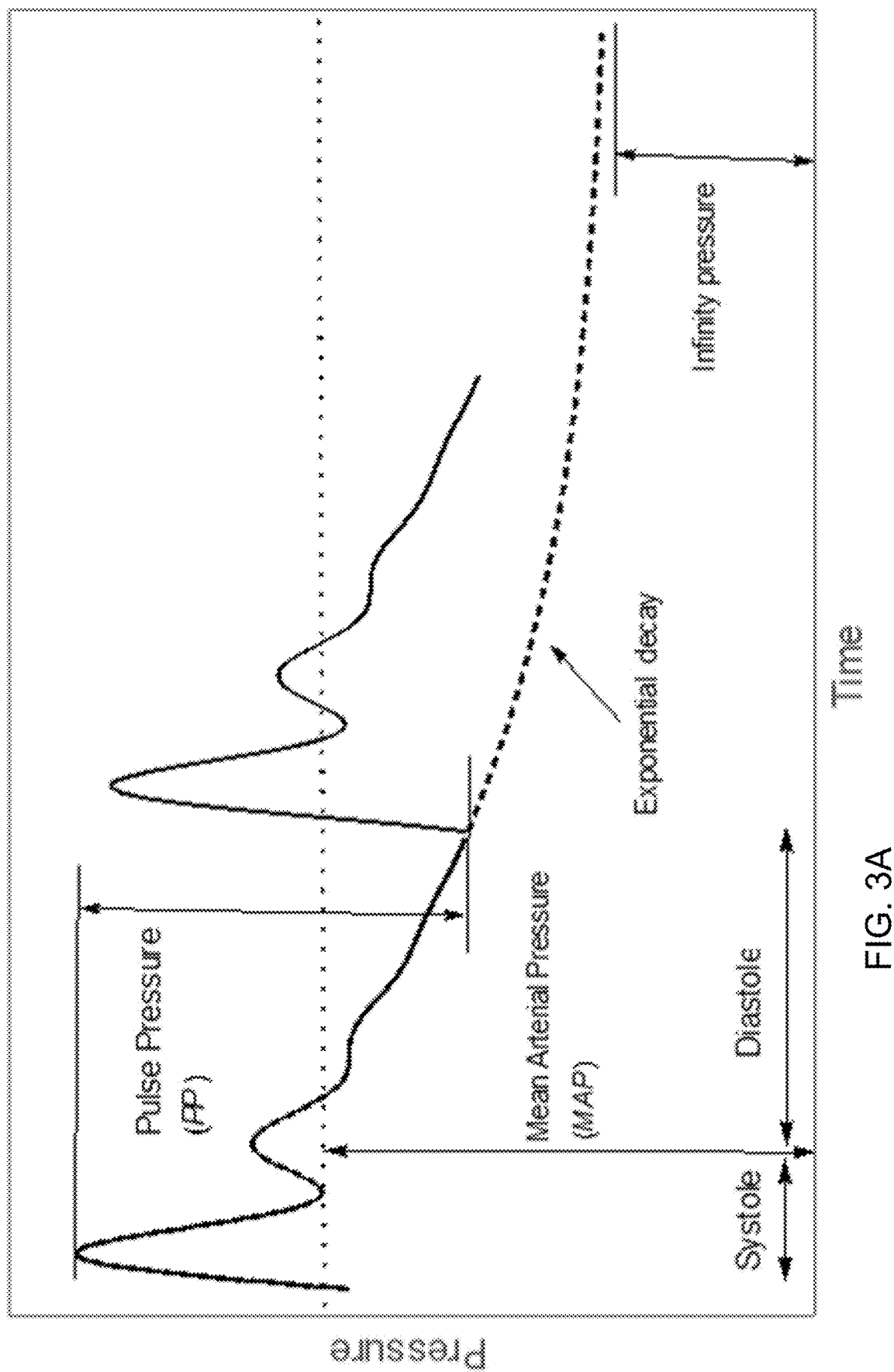
FIG. 3A is a graph of pressure versus time for pulses illustrating essential characteristics of pulses.

FIG. 3A is a graph of an arterial pressure spanning two pulses showing the changes in pressure (i.e., the vertical axis, which may be measured in mmHg) over time (i.e., the horizontal axis, measured in sec). Pressure pulses occur after each contraction of the left heart ventricle and are considered as having three parts.

A first part of an arterial pressure pulse is referred to as the systolic phase, and reflects the immediate rise of the pressure as a consequence of the ejection from the heart, the peaking of the pressure and the onset of the pressure decay.

The second part of an arterial pressure pulse is referred to as the diastolic phase, and reflects the fall of the pressure after the systolic phase. The diastolic phase is generally characterized by an exponentially decaying pressure. The exponential decay asymptotically approaches an infinity pressure, but is redirected before doing so upon the occurrence of the subsequent pulse, which starts the next pulse's systolic phase.

The exponential decay characterizing the diastolic phase may be caused by the arterial system being connected with the veins through the capillary network with a high fluid-flow resistivity and the veins being much more elastic than the arteries. Thus, the veinous system may essentially behave like a large capacitor in relation to the capacitance of the arterial system. Propagation effects may play an insignificant role for the decay since a time-constant of the pressure decay may be much larger than the pulse propagation time through the arterial system. The exponential decay, if uninterrupted by the onset of a subsequent pulse (FIG. 3A), may tend toward an asymptotic value defined as the infinity pressure. The infinity pressure can be inferred from the relative values of the arterial capacitance and the veinous capacitance. The arterial capacitance may be presumed to be proportional to the arterial time constant and the veinous capacitance may be presumed to be proportional to the veinous time constant as described above and in more detail below with reference to FIG. 8. The ratio of the two defines the "infinity ratio". This relationship is illustrated in FIG. 3A as the infinity pressure.

Figure 3B:
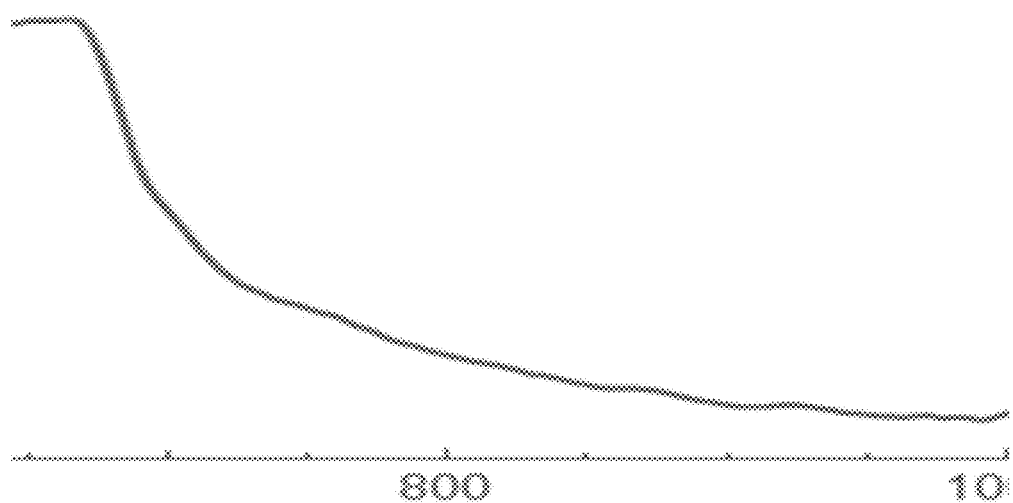
FIG. 3B is a graph of a veinous distension arising from movement of a limb.

FIG. 3B is a graph illustrating vein distension changes (e.g., impedance) resulting from lowering the respective limb. Lowering the limb causes blood to flow into the veins in proximity to the measuring location artery (i.e., arterial draining).

Figure 4A:
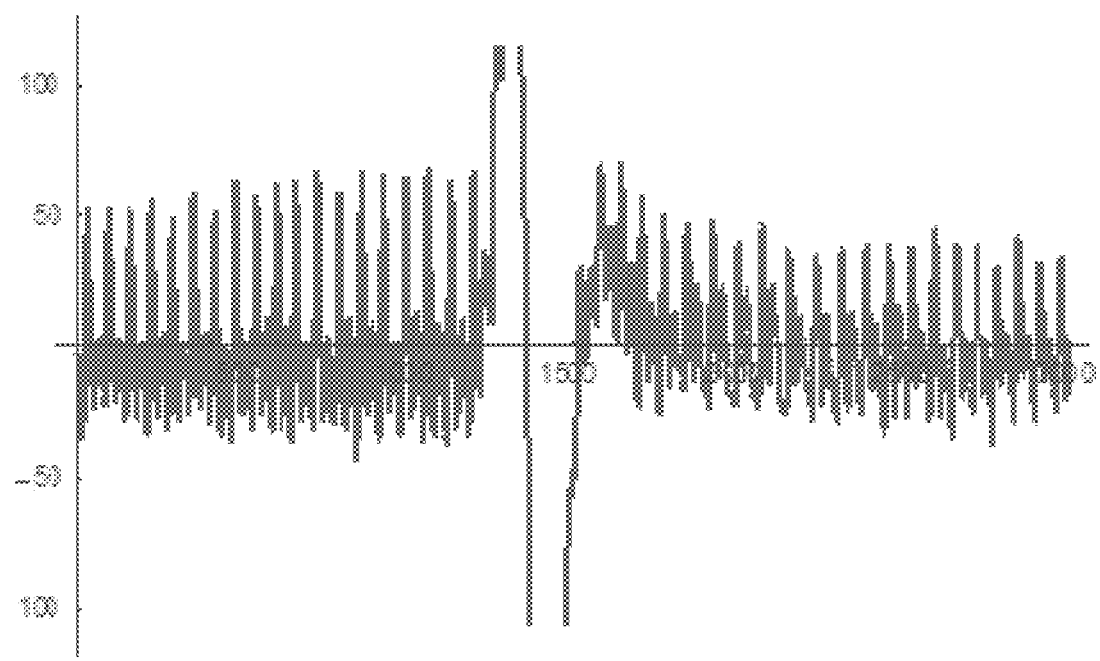
FIGS. 4A, 4B and 5 are graphs illustrating arterial distension and veinous distension within an extremity at heart level and at a lower elevation.
Figure 4B:
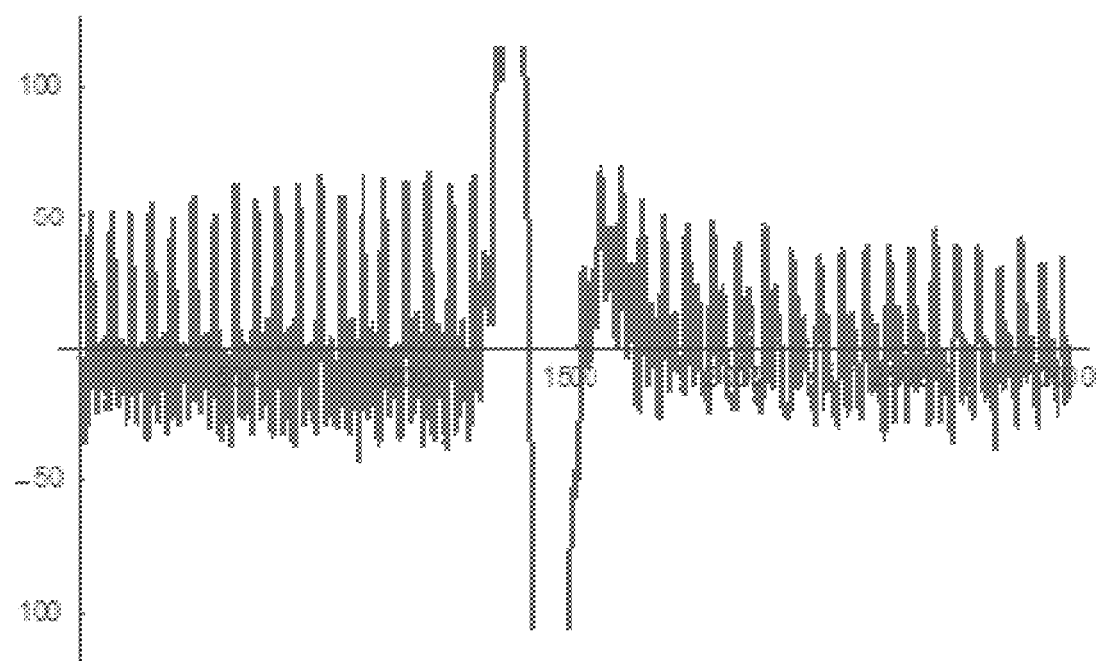
Figure 5:
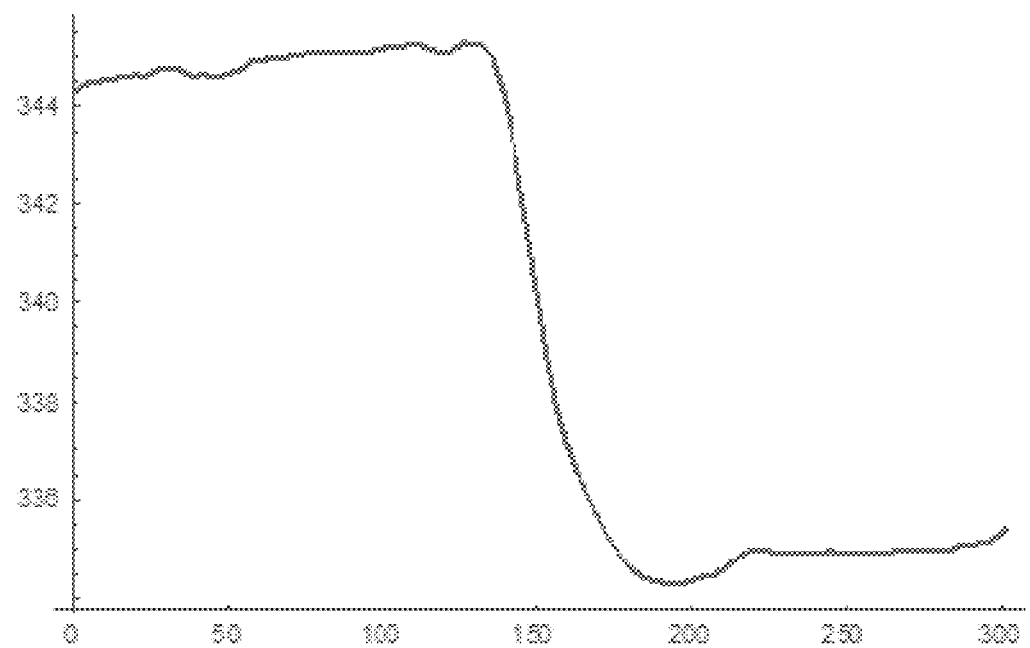

FIGS. 4-5 are graphs of bioimpedance measurements made during one pulse at different elevations of a patient's extremity (a finger). FIG. 4 illustrates the measured impedance associated with arterial distension variations. The spacing between pulses is about one second. The first sequence in FIG. 4 is associated with a measuring location at heart level. The second sequence is associated with the limb oriented straight down. The large transient separating the two sequences may be caused by the movement of the arm from a horizontal position to a downward position. The reduction in transmural pressure may be higher when the limb is positioned at the heart level than at when the limb is oriented in the downward position. This result implies a movement on the stress-strain relation (Equation 5). Details of the diastolic decay for each pulse may be as illustrated in FIG. 3A. Pulse rate, arterial distension amplitudes, δa, as well as arterial time constants and bias terms may be estimated from the pulses of FIG. 4. FIG. 5 illustrates the low-frequency part of the same signal and illustrates an example of bioimpedance measurements measured at an artery in a digit (finger) with the hand at heart level (left side of graph) and with the arm down (right side of graph). A time constant for the filling of the veins surrounding the digital artery can be estimated from FIG. 5. The filling time may be somewhat larger than the pulse spacing in FIG. 4. The ratio of the diastolic arterial time constant and the venous filling (draining) time constant defines the infinity ratio.

The signal representing the venous filling or draining may be obtained by low-pass filtering the sensor signal so that spectral components above the frequency of the heart beat are removed. The heart beat frequency may typically be around 1 Hz, but may be as low as 0.5 Hz or as high as 3 Hz. An alternative to low-pass filtering is to detect the envelope of the low signal amplitude, which correspond to the diastolic phases of the pulses.

Figure 6:
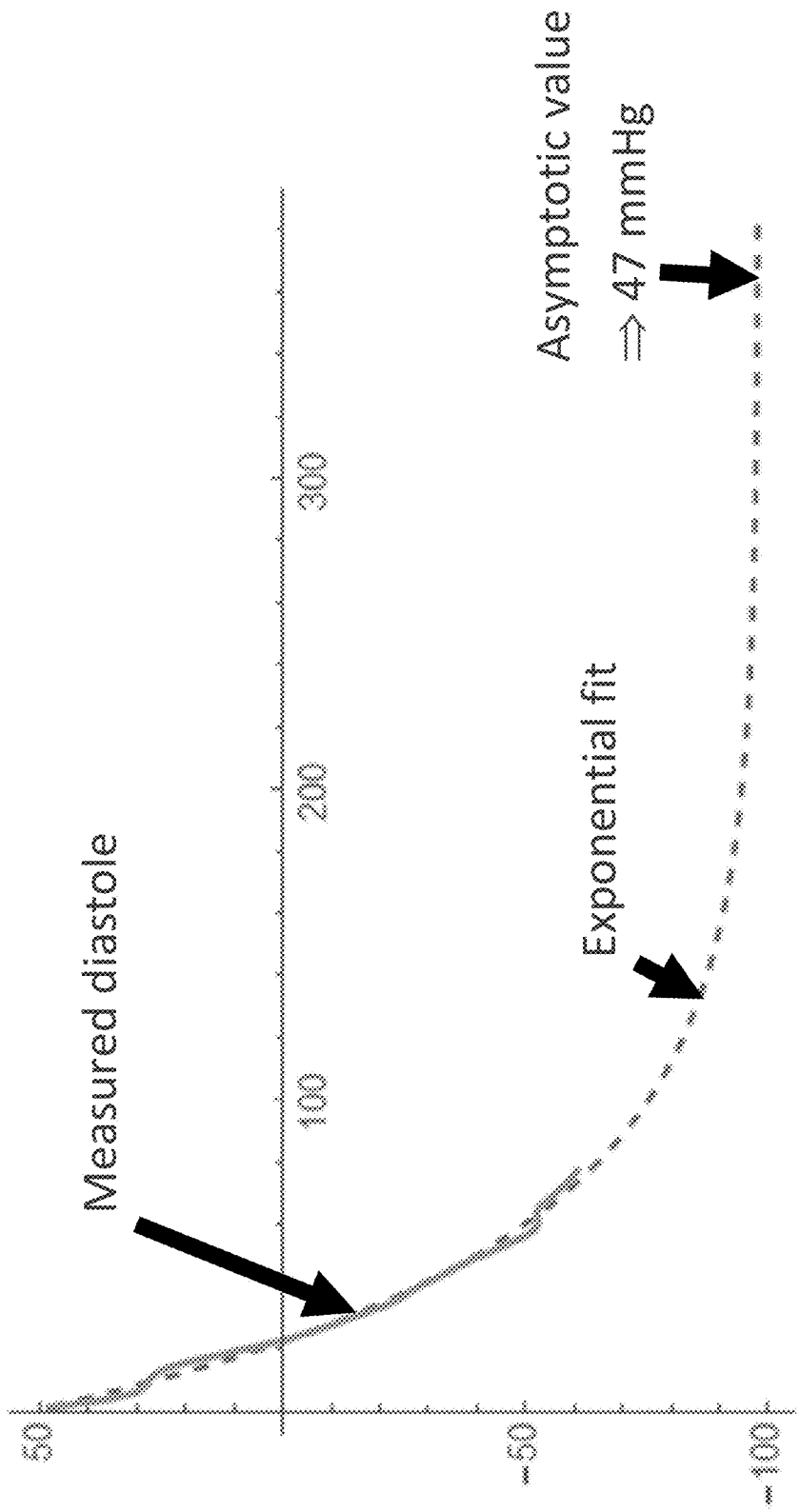
FIG. 6 is a graph of the diastolic portion of a pulse fit to an exponential decay function.

FIG. 6 is a graph of a measurements of arterial distension in the diastolic phase following a pulse (refer to herein as a "distension signal") and an exponential fit (shown in dashed line) to the measurements. FIG. 6 illustrates that measured arterial distension signals during the diastole phase may be modeled using an exponentially decaying function. Appropriate coefficients of such an exponential function may be determined by methods of fitting an exponential function to measurement data. An exponential function fit to the arterial distension measurements may be used to determine an asymptotic value that tends to be greater than zero. The asymptotic value may be converted to pressure, which is 47 mmHg in the example illustrated in FIG. 6. This minimum arterial pressure may be considerably larger than the corresponding veinous pressure. Fitting the arterial distension measurements to an exponential function enables determining the time constant of the function.

Figure 7:
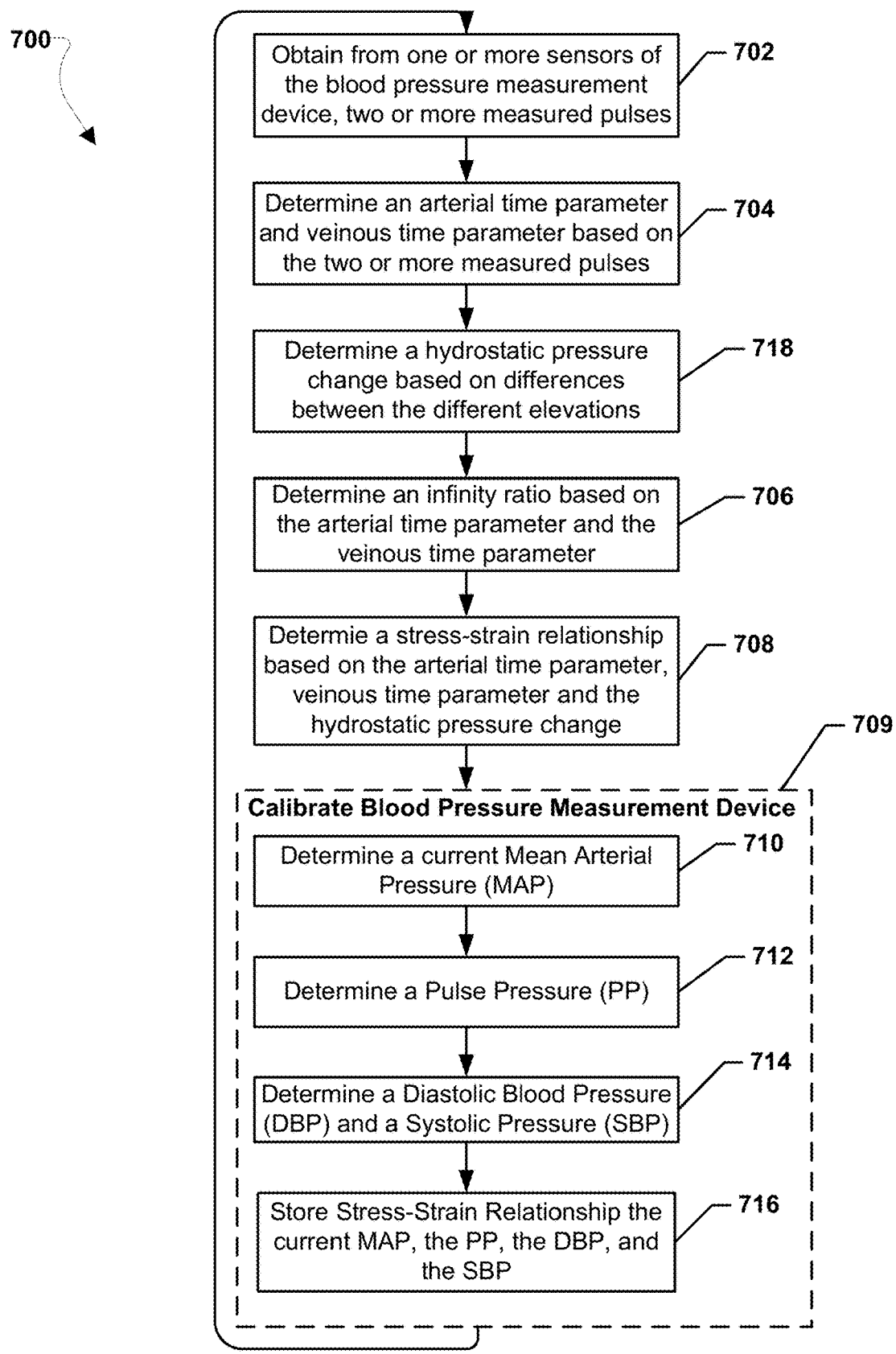
FIG. 7 is a process flow diagram illustrating an embodiment method for calibrating a blood pressure measurement device based on an infinity ratio related to a veinous time constant and an arterial time constant.

FIG. 7 illustrates a method 700 for calibrating a blood pressure measurement device based on measurements of various parameters that enable determining the arterial and veinous time constants from which the infinity ratio may be calculated according to various embodiments. In some embodiments, the operations of method 700 may be performed by a processor of a blood pressure measuring device, such as blood pressure measurement device 100 described above. In other embodiments, the operations of the method 700 may be performed by a processor of another computing device receiving measurements from a blood pressure measuring device. In various embodiments, the operations of the method 700 may be performed by a processor after an initial calibration procedure to set the correct arterial properties for the blood pressure measurement device when a measuring session is started.

In block 702, the processor may obtain from one or more sensors of the blood pressure measurement device, two or more measured pulses (i.e., pulse signals) at a location of measurement on an extremity of a patient where arteries are identified, such as a wrist, finger, arm or leg. In various embodiments, the processor may measure pulses based on outputs from one or more sensors, such as an arterial measurement sensor and an elevation sensor. The pulses may be obtained continuously while the patient raises and/or lowers the body part on which the blood pressure measurement devices positioned. As part of the operations in block 702, elevation may be averaged over a period of a few seconds and typically less than one minute, and the pulses may be averaged over that same period. As part of the operations in block 702, pulses may be recorded continuously as they occur, and the pulse rate may be measured and averaged over a sliding window. Time window for averaging measurements may be between approximately thirty seconds in duration and approximately two minutes in duration.

In block 704, the processor may determine an arterial time parameter and veinous time parameter based on the two or more measured pulse, example method for which is described with reference to FIG. 8.

In block 718, the processor may determine a hydrostatic pressure change based on differences between the different elevations.

In block 706, the processor may determine an infinity ratio based on the arterial time parameter and the veinous time parameter. The infinity ratio may be a representation of the mathematical relationship between the arterial time constant and the veinous time constant. The processor may use the arterial time constant and the veinous time constant obtained in block 704 to calculate the infinity ratio.

In block 708, the processor may determine a stress-strain relationship based on the arterial time parameter, veinous time parameter and the hydrostatic pressure change. The infinity ratio may be used by the processor to evaluate the stress-strain relationship of the measured artery at each measurement height. That is, for each elevation at which the blood pressure measurement device obtains a measurement signal, the processor may evaluate the stress-strain relationship of the artery. By performing evaluations at at least two elevations, the processor may calculate a first parameter $a_0$ as described with reference to equation 7. The second parameter $c_0$ may be determined using the hydrostatic pressure as described with reference to equation 8.

In block 709, the processor may calibrate the blood pressure measuring device based on the stress-strain relationship determined in block 708. Using the infinity ratio, both parameters of the stress-strain relationship may be determined dynamically at the time of calibration. Calculating both parameters of the stress-strain relationship enables the processor to fully define the stress-strain relationship so that blood pressure may be determined in subsequent measurements based on measurement values by applying the defined stress-strain relationship to determine absolute pressure. The operations of which are described in block 710.

In various embodiments, calibrating the blood pressure measurement device in block 709 may include operations for determining different pressures as described with reference to blocks 710-714, and storing such values in memory for subsequent use in block 716 as described below.

In block 710, the processor may determine the current Mean Arterial Pressure (MAP). In various embodiments, the MAP may be calculated by the processor of the blood pressure measuring device. The processor may evaluate the stress-strain relationship at the value of a (i.e., arterial cross-section) determined when the extremity is positioned at the height of the patient's heart.

In block 712, the processor may determine the pulse pressure (PP). In various embodiments, the PP may be calculated by evaluating the incremental variations of the pressure corresponding to the incremental variations of the distension δa around the value of a at the height of the heart. In an embodiment, the PP may be simply obtained by averaging the values of a number of pulses. The number of pulses over which the pulse pressure is averaged may be from one to 60 or more pulses. For general use, pulse pressure may be averaged over 60 pulses since the effect of short term fluctuations may be minimized by such averaging and arterial properties may be generally constant over time periods of one to a few minutes. In the various embodiments, pulse pressure may be determined based at least in part on an exponential stress-strain function of the artillery and vein tissues and measured incremental variations in pressure measurements taken at two elevations.

In block 714, the processor may determine the Systolic Blood Pressure (SBP) and the diastolic blood pressure (DBP). In an embodiment, the MAP and PP may be used to calculate the DBP and SBP in a manner consistent with that described with reference to equations 9 and 10.

In 716, the processor may store the stress-strain relationship, infinity ratio, current MAP, PP, SBP, DBP, and any calculated parameters as calibration parameters maintained in a memory of the blood pressure measurement device. These values may be used during subsequent measurement sessions to determine blood pressure based on a measurement signal. In other words, the processor of the blood pressure measurement device may use the stored calibration parameters in order to convert measured values (e.g., arterial distention) into a blood pressure value.

In various embodiments, calibration of the blood pressure measurement device may be performed periodically including throughout a measurement session, and therefore the processor may return to block 702 to begin the process again.

Figure 8:
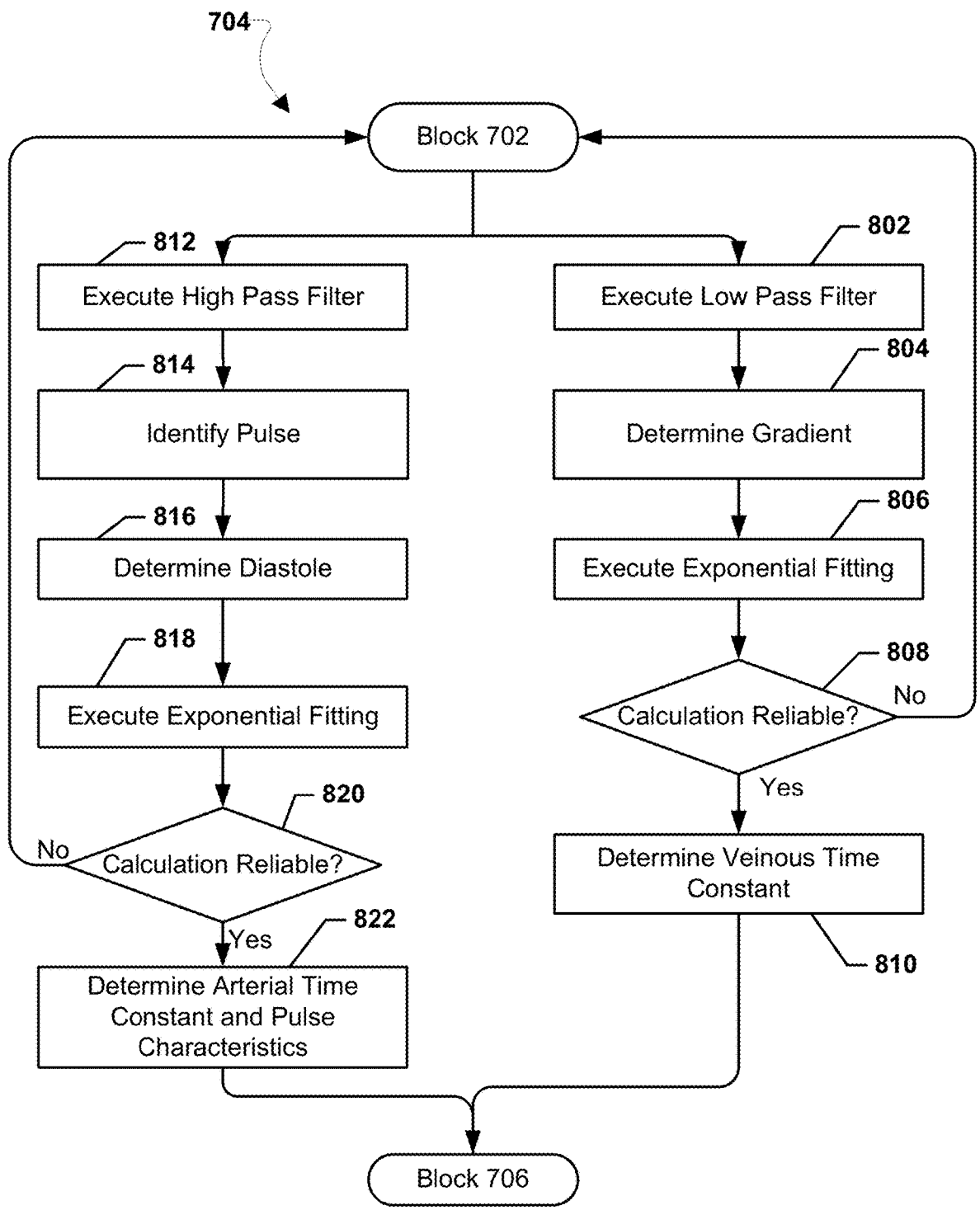
FIG. 8 is a process flow diagram illustrating an embodiment method for calculating an arterial time constant and a veinous time from a measured signal of a non-interfering blood pressure measurement device.

FIG. 8 illustrates a method 704 for calculating a veinous time constant and an arterial time constant for use in determining an infinity ratio according to various embodiments. In some embodiments, the operations of method 704 may be performed by a processor of a blood pressure measuring device, such as blood pressure measurement device 100 described above. In other embodiments, the operations of the method 704 may be performed by a processor of another computing device receiving measurements from a blood pressure measuring device. In various embodiments, the measurement signals may be used to obtain a veinous time constant and an arterial time constant as well as arterial distension. To calculate the arterial time constant and veinous time constant, the processor of the blood pressure measurement device may submit one or more measured signals to both a high pass filter and a low pass filter. In various embodiments, high pass filtering and low pass filtering may be executed in parallel, in series, or in a staggered order.

In various embodiments, the measurement signals obtained in block 702 may be passed as inputs to a low pass filter in block 802 and a high pass filter in block 812. Filtering the measurement signals in blocks 802, 812 may separate the measurement signal into an AC signal component and a quasi-DC signal component. The high-pass and low-pass filters may be wavelet filters and may optionally be configured with a mother wavelet tailored to the expected pulse shape or it may be a fixed Finite Impulse Response (FIR) filter or an Infinite Impulse Response Filter (IIR) as known in the art In block 802, the processor of the blood pressure measuring device may filter one or more measured signals to isolate the portion of the one or more measured signals lying below a threshold frequency, yielding a quasi-DC component of the signal. In various embodiments, the part of a measured signal containing frequency components below the pulse rate (typically 1 Hz) may be extracted, and those components lying above the pulse frequency may be discarded.

In block 804, the processor of the blood pressure measuring device may determine a steepest gradient by analyzing the result of executing the low-pass filter on one or more measured signals. The processor may perform one or more mathematical calculations to determine a portion of the graph of the low-pass filtered signal having the steepest gradient. Such portions may correspond to the time period during which the affected limb transitions from a first measurement height to a second, lower measurement height.

In block 806, the processor of the blood pressure measuring device may perform an exponential fitting analysis to fit an exponential equation to the low-pass filtered measurement signal determined in block 804 to have the steepest gradient. The exponential equation resulting from the execution of the exponential fitting function may be used to determine a veinous time constant (e.g., $\tau_v$).

In determination block 808, the processor of the blood pressure measurement device may determine whether the results of the exponential fitting on the low-pass filtered measurement signal are reliable. For a variety of causes, including muscle movements, rapid changes in pulse rate and measurement noise, a given signal may not be reflective of the subject's veinous filling and draining rate and may include artifacts or be missing measurement portions suitable for obtaining an accurate estimate of the arterial time constant. Therefore, the processor may analyze the raw measurements and/or result of the exponential fitting of particular measurements to identify pulses within the stream of measurements obtained from one or more measurement signals that appear to be representative and thus reliable.

In addition, the processor in determination block 808 may determine whether the result of fitting an exponential equation to the low-pass filtered data performed in block 806 is reliable. For example, results that depart significantly (e.g., one or two standard deviations) from a running average of results from previous pulse measurements may be discarded as likely erroneous.

In response to determining that either the measured signal or the result of the exponential function fitting are not reliable (i.e., block 808="No"), the processor may discard the low-pass filtered measurement signal and may receive the next measurement signal in block 702. In some embodiments, the "next" signal may be received when a change in elevation of the limb occurs.

In response to determining that the result of the exponential function fitting are reliable (i.e., block 808="Yes"), the processor may determine the veinous time constant from the exponential function coefficients in block 810. For example, the veinous time constant may be the exponent (or inverse of the exponent) of the exponential curve determined in block 806. The veinous time constant may change when the elevation of the measuring location is changed, and thus the veinous time constant determined in block 810 may be correlated with the measurement elevation for further use in calculating the infinity ratio in block 706 and other values in method 700 (FIG. 7).

During, before, or after the execution of the operations of blocks 802-810, the processor of the blood pressure measuring device may filter one or more measured signals with a high-pass (high band) filter to isolate the AC portion of the one or more measured signals lying below a threshold frequency in block 812. In various embodiments, executing a high-pass filter on the one or more measurement signals may remove the very low frequency part of the signal, such as the DC-level and the fluctuations on time scales larger than characteristic pulse lengths. The cut-off frequency of the high pass filter may be 2 Hz, 1 Hz or 0.5 Hz or some value within this range. Low-pass filtering may also be incorporated in order to reduce noise with a cut-off frequency typically below 100 Hz such as 60 Hz, 40 Hz, 20 Hz or 10 Hz.

In block 814, the processor of the blood pressure measuring device may identify a pulse within the stream of filtered measurement signals by selecting a specific pulse or portion of a pulse from one or more pulses of the high-pass filtered measurement signal. Individual pulses may be identified following procedures such as using zero crossings with a positive gradient and constrained by limits of accepted pulse length variability. In some embodiments, the pulse(s) identified in block 814 may have a required systolic amplitude within at least one third of the pulse length—typically shorter such as 0.2 sec.). In various embodiments, identifying a pulse may include calculating the amplitude of a pulse as the difference of the maximum and minimum of each pulse, respectively. An average amplitude value for the two levels and for the accepted pulses may be calculated.

In block 816, the processor of the blood pressure measuring device may determine a diastole of the pulse identified in block 814. The diastole may be the diastolic portion of the determined pulse. For pulses exhibiting little oscillation, the diastolic part of the pulse may begin about 0.2 sec after the systolic peak or after the peak following the dicrotic notch until the minimum value (i.e., the tough) of the pulse. For pulses exhibiting a high degree of oscillation, the peaks of oscillations may be fit with the exponential curve. Alternatively, in pulses exhibiting a strong dicrotic notch, a position about 0.2 seconds after the second pulse peak may represent the beginning of the diastolic portion of the pulse signal.

In block 818, the processor of the blood pressure measuring device may execute an exponential fitting function to estimate an exponential curve that fits the diastole determined in block 816. For example, the exponential curve may be an exponential function with a bias term, and may be represented by the expression:

$$f(t,\alpha,\tau_a,\beta)=\alpha \exp[-t/\tau_a]+\beta$$

where the parameters $\{\alpha,\tau_a,\beta\}$ are the amplitude of the determined pulse, the arterial time constant, and the bias term respectively.

In determination block 820, the processor may determine whether the estimated exponential function determined in block 818 is reliable. Not all pulses will be representative of normal pulse and pressure measurements. Also, some results from curve fitting filtered measurement signals to an exponential function may be anomalous, and thus not reliable for use in further calculations. Determinations of whether a pulse measurement signal is not reliable as including muscle or movement artifacts or other reasons may be made in a separate operation and used in both determination blocks 808 and 820. In addition or as an alternative to determining whether a pulse measurement signal is reliable, the processor in determination block 820 may determine whether the result of fitting an exponential equation to the high pass filtered data performed in block 818 is reliable. For example, results that depart significantly (e.g., one or two standard deviations) from a running average of results from previous pulse measurements may be discarded as likely erroneous. For example, if the normalized correlation is above a predetermined value, the processor may determine that the estimated exponential function and associated function coefficients are reliable. The predetermined value may be at least 0.8-0.9. The determination of reliability in determination block 820 may also or alternatively based on a normalized root means square deviation of the results, and the normalized deviation may be at or below 0.2. Methods of identifying reliable pulse measurements may include applying a tailored mother wavelet incorporated into the wavelet transform to the low-pass filtered signals received from the measurement sensor for identifying as valid veinous signals those that correlate to the wavelet transform.

In response to determining that either the measured pulse or the result of the exponential function fitting are not reliable (i.e., block 820="No"), the processor may discard the high-pass filtered measurement signal and retrieve the next measurement signal obtained from the blood pressure sensor in block 702.

In response to determining that the measured pulse and the result of the exponential function fitting are reliable (i.e., block 820="Yes"), the processor may determine the arterial time constant, and pulse characteristics in block 822. For example, the processor may evaluate a mathematical representation of the estimated exponential curve to determine the values for $\{\alpha,\tau_a,\beta\}$. The arterial time constant, the pulse amplitude, and the bias term may be determined based on the evaluation. In some embodiments, the bias term may relate to a pulse level.

Upon obtaining the arterial time constant, the veinous time constant, and the pulse characteristics, the processor of the blood pressure measuring device may use these values in calculating the infinity ratio in block 706 and other values in method 700 (FIG. 7).

In other words, methods of calibrating a blood pressure measurement device may include obtaining a measurement signal (e.g., sensor output, output signal, pulse signal) of an artery of a patient as measured by a non-interfering blood pressure measurement device at different elevations of the non-interfering blood pressure measurement device. The processor of the measurement device may calculate an arterial time constant and a veinous time constant, based on the obtained measurement signal. Further, the processor may calculate an infinity ratio based on the arterial time constant and the veinous time constant. The processor may determine (e.g., by calculating or deriving) multiple parameters characterizing a stress-strain relationship of the artery based on the infinity ratio and a change in hydrostatic pressure. The processor may then calibrate the non-interfering blood pressure measurement device based on the multiple parameters and the stress-strain relationship, such as by calculating multiple pressures that contribute to the absolute blood pressure and storing all calculated quantities and ratios.

Figure 9:
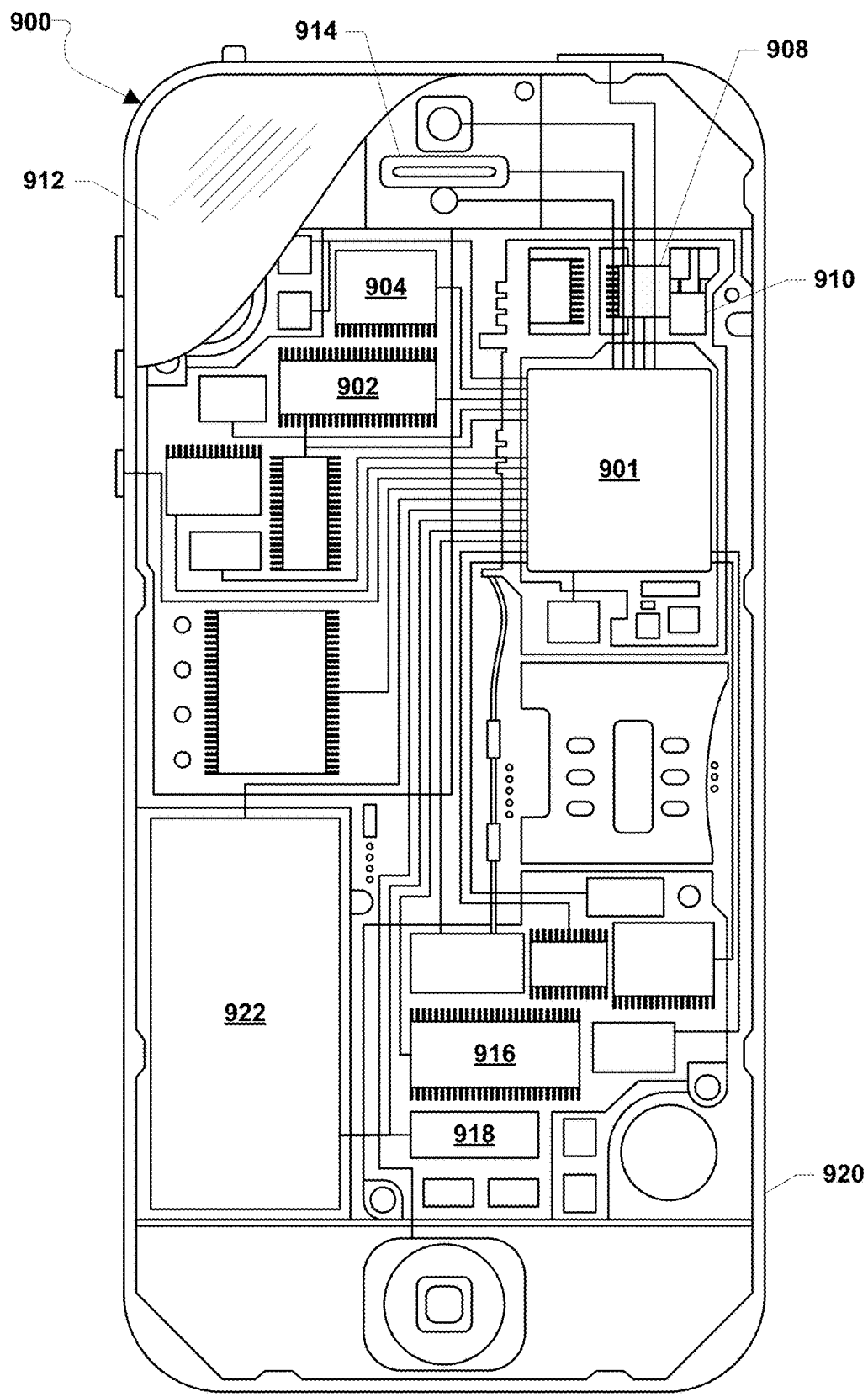
FIG. 9 is a component block diagram of a computing device suitable for use with the various embodiments.

An embodiment blood pressure measurement device may be configured to transmit data to any of a variety of computing devices. For example, FIG. 9 illustrates a computing device 900 suitable for use in various embodiments.

The computing device 900 may exchange data to and/or from the blood pressure measuring devices discussed above, such as pressure measurement device 100, and may perform one or more of the operations of method 700 described above. For example, DBP, PP, SBP, MAP, and/or measured pulses, hydrostatic pressure, measurements of an artery (e.g., measurements related to distension and/or cross sectional area of an artery), and/or elevation may be sent from the blood pressure measurement device to the computing device 900.

In various embodiments, the computing device 900 may include a processor 901 coupled to a touch screen controller 904 and an internal memory 902. The processor 901 may be one or more multicore ICs designated for general or specific processing tasks. The internal memory 902 may be volatile or non-volatile memory, and may also be secure and/or encrypted memory, or unsecure and/or unencrypted memory, or any combination thereof. The touch screen controller 904 and the processor 901 may also be coupled to a touch screen panel 912, such as a resistive-sensing touch screen, capacitive-sensing touch screen, infrared sensing touch screen, etc. The computing device 900 may have one or more radio signal transceivers 908 (e.g., Peanut®, Bluetooth®, Zigbee®, Wi-Fi, RF, cellular, etc.) and antennae 910, for sending and receiving, coupled to each other and/or to the processor 901. The transceivers 908 and antennae 910 may be used with the above-mentioned circuitry to implement the various wireless transmission protocol stacks and interfaces. The computing device 900 may include a cellular network wireless modem chip 916 that enables communication via a cellular network, such as an eMBMS network, and is coupled to the processor. The computing device 900 may include a peripheral device connection interface 918 coupled to the processor 901. The peripheral device connection interface 918 may be singularly configured to accept one type of connection, or multiply configured to accept various types of physical and communication connections, common or proprietary, such as USB, FireWire, Thunderbolt, or PCIe. The peripheral device connection interface 918 may also be coupled to a similarly configured peripheral device connection port (not shown). The computing device 900 may also include speakers 914 for providing audio outputs. The computing device 900 may also include a housing 920, constructed of a plastic, metal, or a combination of materials, for containing all or some of the components discussed herein. The computing device 900 may include a power source 922 coupled to the processor 901, such as a disposable or rechargeable battery. The rechargeable battery may also be coupled to the peripheral device connection port to receive a charging current from a source external to the computing device 900.

Processors of computing devices suitable for use in various embodiments may be any programmable microprocessor, microcomputer or multiple processor chip or chips that can be configured by software instructions (applications) to perform a variety of functions, including the functions of the various embodiments described above. In the various devices, multiple processors may be provided, such as one processor dedicated to wireless communication functions and one processor dedicated to running other applications. Typically, software applications may be stored in internal memory before they are accessed and loaded into the processors. The processors may include internal memory sufficient to store the application software instructions. In many devices, the internal memory may be a volatile or nonvolatile memory, such as flash memory, or a mixture of both. For the purposes of this description, a general reference to memory refers to memory accessible by the processors including internal memory or removable memory plugged into the various devices and memory within the processors.

Further, those of skill in the art will appreciate that the foregoing method descriptions and the process flow diagrams are provided merely as illustrative examples and are not intended to require or imply that the operations of the various embodiments must be performed in the order presented. As will be appreciated by one of skill in the art the order of operations in the foregoing embodiments may be performed in any order. Words such as "thereafter," "then," "next," etc. are not intended to limit the order of the operations; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope embodiments.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

The functions in the various embodiments may be implemented in hardware, software, firmware, or any combination thereof. If implemented in software, the functions may be stored as one or more processor executable instructions or code on a non-transitory computer readable medium or non-transitory processor readable medium. The operations of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the present invention is not intended to be limited to the embodiments shown herein but is to be accorded the widest scope consistent with the following claims and the principles and novel features disclosed herein.

What is claimed is:

1. A method executed by a blood pressure measurement device for calibrating the blood pressure measurement device positioned on a body of subject during a blood pressure measuring session of the subject being conducted by the blood pressure measurement device including one or more processors and one or more sensors, the method comprising:
    measuring, by the one or more sensors, two or more blood pressure pulses, wherein at least one measured pulse from the two or more measured pulses correspond to a first elevation of the one or more sensors of the blood pressure measurement device and at least one measured pulse from the two or more measured pulses correspond to a second elevation of the one or more sensors of the blood pressure measurement device, wherein the second elevation is different than the first elevation;
    determining, by the one or more processors, an arterial time parameter and a veinous time parameter based on the at least one measured pulse corresponding to the first elevation and the at least one measured pulse corresponding to the second elevation;
    determining, by the one or more processors, a hydrostatic pressure change based on a difference between the at least one measured pulse at the first elevation and the at least one measured pulse at the second elevation;
    determining, by the one or more processors, an infinity ratio from the arterial time parameter and the veinous time parameter;
    determining, by the one or more processors, a stress-strain relationship based on at least the determined hydrostatic pressure change and the determined infinity ratio; and
    calibrating the blood pressure measurement device by applying, by the one or more processors, the stress-strain relationship to a blood pressure measuring session conducted by the blood pressure measurement device.

2. The method of claim 1, wherein applying the stress-strain relationship to the blood pressure measuring session comprises:
    determining, by the one or more processors, a current mean arterial pressure based at least in part on the stress-strain relationship;
    determining, by the one or more processors, a pulse pressure based at least in part on the stress-strain relationship and a variation in pressure between the first elevation and the second elevation;
    determining, by the one or more processors, a diastolic blood pressure and a systolic blood pressure based on the current mean arterial pressure and the pulse pressure; and
    storing, by the one or more processors, the stress-strain relationship, the current mean arterial pressure, the pulse pressure, the diastolic blood pressure, the systolic blood pressure or any combination thereof.

3. The method of claim 1, wherein the two or more measured pulses are measured using one or more of bioimpedance, impedance plethysmography, photoplethsmography, ultrasound or any combination thereof.

4. The method of claim 1, wherein the determining, by the one or more processors, the veinous time parameter includes:
    filtering the two or more measured pulses using a low-pass filter;
    identifying, by the one or more processors, a portion of the low-pass filtered two or more measured pulses corresponding to a transition between the first elevation and the second elevation;
    fitting, by the one or more processors, an exponentially decaying function to the identified portion of the low-pass filtered two or more measured pulses; and
    determining the veinous time parameter based on the exponentially decaying function.

5. The method of claim 1, wherein the determining, by one or more processors, the arterial time parameter includes:
    filtering the two or more measured pulses using a high pass filter;
    determining, by the one or more processors, a diastole portion of the high-pass filtered two or more measured pulses;
    fitting, by the one or more processors, an exponentially decaying function to the diastole portion of the high-pass filtered two or more measured pulses; and
    determining, by the one or more processors the arterial time parameter based on the exponentially decaying function.

6. The method of claim 1, wherein the first elevation is at or below a heart level of the subject and the second elevation is lower in height than the first elevation.

7. The method of claim 1, wherein the infinity ratio is based on a first elevation infinity ratio calculated from a determination of the arterial time parameter and the veinous time parameter from the a least one measured pulse corresponding to the first elevation, and a second elevation infinity ratio calculated from a determination of the arterial time parameter and the veinous time parameter from the at least one measured pulse corresponding to the second elevation.

8. The method of claim 7, wherein the infinity ratio is calculated as an average of the first elevation infinity ratio and the second elevation infinity ratio.

9. A blood pressure measurement device, comprising:
    one or more arterial measurement sensors configured to obtain two or more blood pressure pulses, wherein at least one measured pulse from the two or more measured pulses correspond to a first elevation of the one or more arterial measurement sensors of the blood pressure measurement device and at least one measured pulse from the two or more measured pulses correspond to a second elevation of the one or more arterial measurement sensors of the blood pressure measurement device, wherein the second elevation is different from the first elevation;

one or more elevation sensors configured to determine the first elevation of the one or more arterial measurement sensors and the second elevation of the one or more arterial measurement sensors; and one or more processors coupled to the one or more arterial measurement sensors and the one or more elevation sensors to calibrate the blood pressure measurement device when the blood pressure measurement device is positioned on a body of a subject during a blood pressure measuring session of the subject being conducted by the blood pressure measurement device, wherein the one or more processors are configured to:

determine an arterial time parameter and veinous time parameter based on the at least one measured pulse corresponding to the first elevation and the at least one measured pulse corresponding to the second elevation;

determine a hydrostatic pressure change based on a difference between the at least one measured pulse at the first elevation and the at least one measured pulse at the second elevation;

determine an infinity ratio from the arterial time parameter and the veinous time parameter;

determine a stress-strain relationship based on at least the determined hydrostatic pressure change and the determined infinity ratio; and calibrate the blood pressure measurement device by applying the determined stress-strain relationship to a blood pressure measuring session conducted by the blood pressure measurement device.

10. The blood pressure measurement device of claim 9, wherein the one or more processors are further configured to:

determine a current mean arterial pressure based at least in part on the stress-strain relationship;

determine a pulse pressure based at least in part on the stress-strain relationship and a variation in pressure between the first elevation and the second elevation;

determine a diastolic blood pressure and a systolic blood pressure based on the current mean arterial pressure and the pulse pressure; and store the stress-strain relationship, the current mean arterial pressure, the pulse pressure, the diastolic blood pressure, the systolic blood pressure or any combination thereof.

11. The blood pressure measurement device of claim 9, wherein the one or more arterial measurement sensors comprise one or more of a bioimpedance sensor, impedance plethysmography sensor, photoplethsmography sensor, ultrasound sensor, or any combination thereof.

12. The blood pressure measurement device of claim 9, wherein the one or more processors are further configured to determine the veinous time parameter by:

filtering the two or more measured pulses using a low-pass filter;

identifying a portion of the low-pass filtered two or more measured pulses corresponding to a transition between the first elevation and the second elevation;

fitting an exponentially decaying function to the identified portion of the low-pass filtered two or more measured pulses; and determining the veinous time parameter based on the exponentially decaying function.

13. The blood pressure measurement device of claim 9, wherein the one or more processors are further configured to determine the arterial time parameter by:

filtering the two or more measured pulses using a high pass filter;

determining a diastole portion of the high-pass filtered two or more measured pulses;

fitting an exponentially decaying function to the diastole portion of the high-pass filtered two or more measured pulses; and determining the arterial time parameter based on the exponentially decaying function.

14. The blood pressure measurement device of claim 9, wherein the first elevation is at or below a heart level of the subject and the second elevation is lower in height than the first elevation.

15. The blood pressure measurement device of claim 9, wherein the infinity ratio is based on a first elevation infinity ratio calculated from a determination of the arterial time parameter and the veinous time parameter from the at least one measured pulse corresponding to the first elevation, and a second elevation infinity ratio calculated from a determination of the arterial time parameter and the veinous time parameter from the at least one measured pulse corresponding to the second elevation.

16. The blood pressure measurement device of claim 15, wherein the one or more processors are configured to calculate the infinity ratio as an average of the first elevation infinity ratio and the second elevation infinity ratio.

17. A blood pressure measurement device operable to calibrate the blood pressure measurement device when positioned on a body of a subject during a blood pressure measuring session of the subject being conducted by the blood pressure measurement device, the blood measurement device comprising:

measurement means for measuring two or more blood pressure pulses, wherein at least one measured pulse from the two or more measured pulses correspond to a first elevation of the measurement means of the blood pressure measurement device and at least one measured pulse of the two or more measured pulses correspond to a second elevation of the measurement means of the blood pressure measurement device, wherein the second elevation is different than the first elevation;

means for determining an arterial time parameter and a veinous time parameter based on the at least one measured pulse corresponding to the first elevation and the at least one measured pulse corresponding to the second elevation;

means for determining a hydrostatic pressure change based on a difference between the at least one measured pulse at the first elevation and the at least one measured pulse at the second elevation;

means for determining an infinity ratio of the arterial time parameter to the veinous time parameter;

means for determining a stress-strain relationship based on the arterial time parameter, the veinous time parameter and at least the determined hydrostatic pressure change and the determined infinity ratio; and means for calibrating the blood pressure measurement device by applying the stress-strain relationship to a blood pressure measuring session conducted by the blood pressure measurement device.

18. The blood pressure measurement device of claim 17, further comprising:

means for determining a current mean arterial pressure based at least in part on the stress-strain relationship;

means for determining a pulse pressure based at least in part on the stress-strain relationship and variation in pressure between the first elevation and the second elevation;

means for determining a diastolic blood pressure and a systolic blood pressure based on the current mean arterial pressure and the pulse pressure; and means for storing the stress-strain relationship, the current mean arterial pressure, the pulse pressure, the diastolic blood pressure, the systolic blood pressure or any combination thereof.

\* \* \* \* \*